United States Patent [19]
Scott et al.

[11] Patent Number: 5,955,653
[45] Date of Patent: Sep. 21, 1999

[54] CALLASE-RELATED DNAS AND THEIR USE IN ARTIFICIAL MALE STERILITY

[75] Inventors: Roderick John Scott; John Draper; Wyatt Paul, all of Leicester, United Kingdom

[73] Assignee: Biogemma UK Limited, Cambridge, United Kingdom

[21] Appl. No.: 08/185,828

[22] PCT Filed: Jul. 23, 1992

[86] PCT No.: PCT/GB92/01354

§ 371 Date: Mar. 23, 1994

§ 102(e) Date: Mar. 23, 1994

[87] PCT Pub. No.: WO93/02197

PCT Pub. Date: Feb. 4, 1993

[30] Foreign Application Priority Data

Jul. 23, 1991 [GB] United Kingdom ............ 9115909

[51] Int. Cl.$^6$ ............ A01H 5/00; C12N 15/29; C12N 15/56; C12N 15/82

[52] U.S. Cl. ............ 800/303; 800/287; 800/298; 800/300; 536/23.6; 536/24.1; 435/200; 435/209; 435/320.1; 435/418; 435/419; 435/468

[58] Field of Search ............ 536/23.6, 24.1; 530/370; 435/172.3, 240.4, 320.1, 419, 200, 418, 209, 468; 800/205, 250, 287, 298, 300, 303

[56] References Cited

FOREIGN PATENT DOCUMENTS

| | | |
|---|---|---|
| 344029 | 11/1989 | European Pat. Off. . |
| 392225 | 10/1990 | European Pat. Off. . |
| 418695 | 3/1991 | European Pat. Off. . |
| 90 08828 | 8/1990 | WIPO . |
| 92 11379 | 7/1992 | WIPO . |

OTHER PUBLICATIONS

Paul, W., et al., "Aspects of the molecular biology of anther development," J. Exp. Bot. . Annual Meeting of the Society for Experimental Biology, Birmingham, AL, Apr. 7–12, 1991, vol. 42, 1991, 238 Suppl. p. 40.

Scott, R., et al. "Identification of genes exhibiting cell–specific and temporal regulation in developing anthers of Brassica–napus," J. Exp. Botany, 1990 Annual Meeting of the Society for Experimental Biology, vol. 41, 1990 suppl., p. P5–3.

Barghchi, M., et al., "Genetic engineering of Arabidopsis," Abstracts VIIth International Congress on Plant Tissues and Cell Culture, 1990, Jun. 24–29, Amsterdam, p. 46, Abstract No. A2–10.

Scott, R. et al., "Patterns of gene expression in developing anthers of Brassica napus," Plant Molecular Biology, vol. 17, No. 2, 1991, pp. 195–207.

Del Campillo, E. et al., "Cell wall hydrolases in anther and abscission zones," Plant Phisiology Supplement, Annual Meeting American Society of Plant Physiologists, Jul. 29–Aug. 2, 1990, vol. 93, No. 1, May 1990, Abstract No. 771.

Hodge, R. P. et al., "A9—a tapetum specific gene," J. Expermental Botany, Annual Meeting of the Society for Experimental Biology, Birmingham, AL, Apr. 7–12, 1991, vol. 238, 1991, Suppl. p. 40.

Mascavenhas, J. 1989. Mol. Basis Plant Dev., Goldberg, R.,ed., Alan R. Liss, Inc.: New York, pp. 99–105.

Worrall et al 1992 (Jul.) The Plant Cell 4:759–771.

Krabel et al 1993 Plant Science 93:19–23.

*Primary Examiner*—David T. Fox
*Attorney, Agent, or Firm*—Hale and Dorr LLP

[57] ABSTRACT

A tapetum-specific callase (β-1,3-glucanase) gene, designated A6, from *Brassica napus* and other members of the family Brassicaceae including *A. thaliana* has been discovered, isolated and cloned. The A6 gene encodes a 53 kDa callase enzyme of *Brassica napus* and equivalent proteins in other Brassicaceae family members. Coding sequence from the gene can be driven by an appropriate promoter to induce male sterility in plants. Further, the A6 promoter can be used to drive male sterility DNA such as that coding for a nuclease, protease or glucanase. Alternatively or in addition, male sterility can be achieved by disrupting the proper expression of the A6 gene, for example by transcribing RNA which is antisense to the RNA normally transcribed from the A6 gene, or by expressing DNA coding for a ribozyme specific for the A6 gene RNA transcript.

20 Claims, 39 Drawing Sheets

DNA sequence of Brassica napus cDNA A6 and the deduced protein sequence of the ORF within A6.

```
     F   F   L   F   T   L   V   V   F   S   S   T   S   C   S   A   V   G   F
    CTTTCTTCCTCTTCACCCTCGTCGTCTTTTCAAGTACAAGTTGCTCAGCGGTTGGGTTCC
             10        20        30        40        50        60

Q   H   P   H   R   Y   I   Q   K   K   T   M   L   E   L   A   S   K   I   G
    AACATCCGCACAGGTATATACAGAAAAAAACGATGCTAGAGTTAGCCAGCAAGATTGGTA
             70        80        90       100       110       120

I   N   Y   G   R   Q   G   N   N   L   P   S   P   Y   Q   S   I   N   F   I
    TTAACTATGGTAGACAAGGAAACAACCTACCTCCTTACCAATCGATCAATTTCATCA
            130       140       150       160       170       180

K   L   I   K   A   G   H   V   K   L   Y   D   A   D   P   E   S   L   T   L
    AACTCATCAAAGCCGGTCATGTCAAGCTCTACGACGCCGATCCAGAGAGTCTAACACTCC
            190       200       210       220       230       240
```

FIG. 1a

| FIG. 1a |
|---|
| FIG. 1b |
| FIG. 1c |
| FIG. 1d |
| FIG. 1e |
| FIG. 1f |

FIG. 1

```
L  S  Q  T  N  L  Y  V  T  I  A  V  P  T  H  Q  I  T  S  L
TCTCTCAAACCAATCTCTACGTCACCATAGCCGTGCCAACCCACCAGATCACTTCCCTCA
         250               260               270               280               290               300

S  A  N  Q  T  T  A  E  D  W  V  K  T  N  I  L  P  Y  Y  P
GCGCCAACCAAACTACAGCTGAAGATTGGGTCAAAAACCAATATCCTCCCTTACTACCCAC
         310               320               330               340               350               360

Q  T  Q  I  R  F  V  L  V  G  N  E  I  L  S  V  K  D  R  N
AAACACAAATACGATTTGTCCTTGTTGGAAACGAAATCCTCTCCGTCAAAGATAGGAACA
         370               380               390               400               410               420

I  T  G  N  V  V  P  A  M  R  K  I  V  N  S  L  R  A  H  G
TAACCGGCAATGTCGTACCGGCAATGCGAAAAATCGTGAACTCTCTCAGAGCCCATGGGA
         430               440               450               460               470               480

I  H  N  I  K  V  G  T  P  L  A  M  D  S  L  R  S  T  F  P
TTCACAACATCAAAGTCGGTACACCTTTAGCTATGGATTCTCTTCGATCAACGTTTCCGC
         490               500               510               520               530               540
```

FIG. 1b

```
        P  S  N  S  T  F  R  G  D  I  A  L  P  L  M  L  P  L  L  K
        CGTCGAACTCAACATTCCGGGGAGATATCGCCCTTACCGTTAATGTTGCCGTTGCTGAAGT
                 550          560          570          580          590          600

F  L  N  G  T  N  S  Y  F  F  I  N  L  Q  P  Y  F  R  W  S
        TTCTCAACGGAACAAACTCTTACTTCTCTTTATCAATCTTCAACCTTACTTCCGTTGGTCAA
                 610          620          630          640          650          660

R  N  P  N  H  T  T  L  D  F  A  L  F  Q  G  N  S  T  Y  T
        GAAACCCTAATCACACCACCGTTGGATTTCGCTCTGTTTCAAGGAAACTCAACTTATACCG
                 670          680          690          700          710          720

D  P  H  T  G  L  V  Y  H  N  L  V  D  Q  M  L  D  S  V  I
        ATCCTCATACCGGTTTGGTTTACCATAATCTTGTAGACCAAATGTTGGATTCGGTTATCT
                 730          740          750          760          770          780

F  A  M  T  K  L  G  Y  P  Y  I  R  I  A  I  S  E  T  G  W
        TCGCCATGACCAAGCTCGGTTATCCATACATCCGTATCGCAATCTCTGAAACCGGGATGGC
                 790          800          810          820          830          840
```

FIG. 1c

```
  P  N  S  G  D  I  D  E  I  G  A  N  V  F  N  A  A  T  Y  N
CTAACTCCGGCGACATCGACGAAATCGGAGCTAACGTTTCAACGCCGCCACGTATAACC
           850        860        870        880        890        900

R  N  L  I  K  K  M  T  A  T  P  P  I  G  T  P  A  R  P  G
GGAATTTGATCAAGAAGATGACCGCAACTCCACCAGTACACCAGCTAGACCCGGTT
           910        920        930        940        950        960

S  P  I  P  T  F  V  F  S  L  F  N  E  N  K  K  P  G  S  G
CACCTATACCGACATTTGTTTTCTCCTTATTTAACGAAAACAAGAAACCCGGTTCGGGAA
           970        980        990       1000       1010       1020

T  Q  R  H  W  G  I  L  H  P  D  G  T  P  I  Y  D  I  D  F
CACAAAGACATTGGGGAATCTTGCATCCGGACGGTACACCAATCTACGACATTGATTTTA
          1030       1040       1050       1060       1070       1080

T  G  Q  K  P  L  T  G  F  N  P  L  P  K  P  T  N  N  V  P
CCGGTCAAAAACCCCTTAACCGGTTTTAACCCCTCTGCCTAAAACCGACGAATAACGTTCCTT
          1090       1100       1110       1120       1130       1140
```

FIG. 1d

```
Y   K   G   Q   V   W   C   V   P   V   E   G   A   N   E   T   E   L   E   E   E
ACAAGGGTCAAGTGTGGTGCGTACCGGTGCCGAAGGAGCCAACGAGACTGAGCTCGAGGAAG
         1150                1160                1170                1180                1190                1200

A   L   R   M   A   C   A   R   S   N   T   T   C   A   A   L   V   P   G   R
CTTTGAGGATGGCTTGTGCCCGAAGCAACACGACGTGTGCGGCTTTGGTTCCTGGCAGAG
         1210                1220                1230                1240                1250                1260

E   C   Y   E   P   V   S   V   Y   W   H   A   S   Y   A   L   N   S   Y   W
AATGTTACGAGCCGGTCTCTGTTTATTGGCACGCAAGCTACGCGCTTAACTCGTACTGGG
         1270                1280                1290                1300                1310                1320

A   Q   F   R   S   Q   N   V   Q   C   Y   F   N   G   L   A   H   E   T   T
CACAGTTCCGTAGCCAAAACGTTCCAATGTTACTTCAATGGATTAGCTCATGAGACCACGA
         1330                1340                1350                1360                1370                1380
```

FIG. 1e

```
 T   N   P   G   N   D   R   C   K   F   P   S   V   T   L   *
CTAACCCTGGAAATGATCGGCTGCAAGTTCCGAGCGTTACTCTGTGAGGAAGAACGCCTG
         1390          1400          1410          1420          1430          1440

AAAGAGATTTAAGATGATCAAAGCTGGATTATTCGTATTTACTCTCATTCTAGATTTCTGG
         1450          1460          1470          1480          1490          1500

TTTCTGTTTCGTGTGGCCCTAATGTTGAGAAAA
         1510          1520          1530
```

FIG. 1f

Alignment of the deduced primary structures of the B.napus and the A.thaliana A6 genes with the primary structure of previously described glucanases.

```
*  :=>  match across all seqs.
.  :=>  conservative substitutions
```

```
NPGLUC                                        ALQMAAIILLGLIVSSTEIVGAQSVGVCYGMLGNNLPPASQV
BEAN                                                                    QIGVCYGMGNNLPSANEV
PR-Q       QFLFSLQMAHLIVTLLLLSVLTLATLDFTGAQAGVCYGRQGNGLPSPADV
BARLEY            MARKDVASMFAAALFIGAFAAVPTSVQSIGVCYGVIGNNLPSRSDV
At G62     MSLLAFFLFTILVFSSSCCSATRFQ-GHRYMQRKTMLDLASKIGINYGRRGNNLPSPYQS
Bn A6            FFLFTLVVFSSTSCSAVGFQHPHRYIQKKTMLELASKIGINYGRQGNNLPSPYQS
                                                     *  ** **  ** *  .

NPGLUC     VQLYKSKNIRRMRLYDPNQAALQALRGSNIEVMLGVPNSDLQNIAANPSNANNWVQRNVR
BEAN       INLYRSNNIRRMRLYDPNGAALGALRNSGIELILGVPNSDLQGLATNADTARQWVQRNVL
PR-Q       VSLCNRNNIRRMRIYDPDQPTLEALRGSNIELMLGVPNPDLENVAASQANADTWVQNNVR
BARLEY     VQLYRSKGINGMRIYFADGQALSALRNSGIGLILDIGNDQLANIAASTSNAASWVQNNVR
At G62     INFIKSIKAGHVKLYDADPESLTLLSQTNLYVTITVPNHQITALSSNQTIADEWVRTNIL
Bn A6      INFIKLIKAGHVKLYDADPESLTLLSQTNLYVTIAVPTHQITSLSANQTTAEDWVKTNIL
                 * *          *          *        **  **   .
```

FIG. 2a

| FIG. 2a |
|---------|
| FIG. 2b |
| FIG. 2c |
| FIG. 2d |
| FIG. 2e |

FIG. 2

```
NPGLUC    NFWPAVKFRYIAVGNEVSPVTGTSSLTRYLLPAMRNIRNAISSAGLQNNIKVSSSVDMTL
BEAN      NFWPSVKIKYIAVGNEVSPVGGSSWYAQYVLPAVQNVYGAVRAQGLHDGIKVSTAIDMTL
PR-Q      NY-GNVKFRYIAVGNEVSPLNENSKYVPVLLNAMRNIQTAISGAGLGNQIKVSTAIETGL
BARLEY    PYYPAVNIKYIAAGNEVQGGA----TQSILPAMRNLNAALSAAGLG-AIKVSTSIRFDE
At G62    PYYPQTQIRFVLVGNEILSYNSGN-VSVNLVPAMRKIVNSLRLHGIHN-IKVGTPLAMDS
Bn A6     PYYPQTQIRFVLVGNEILSVKDRN-ITGNVVPAMRKIVNSLRAHGIHN-IKVGTPLAMDS
                  . *        *  ..  .   . .    *  ***    .

NPGLUC    IGNSFPPSQGSFRNDVR-SFIDPIIGFVRRINSPLLVNIYPYFSYAGNPRDISLPYALFT
BEAN      IGNSYPPSQGSFRGDVR-SYLDPIIGYLLYASAPLHVNVYPYFSYSGNPRDISLPYALFT
PR-Q      TTDTSPPSNGRFKDDVR-QFIEPIINFLVTNRAPLLVNLYPYFAIANNA-DIKLEYALFT
BARLEY    VANSFPPSAGVFKN----AYMTDVARLLASTGAPLLANVYPYFAYRDNPGSISLNYATFQ
At G62    LRSSFPRSNGTFREEITGPVMLPLLKFLNGTNSYFFLNVHPYFRWSRNPMNTSLDFALFQ
Bn A6     LRSTFPPSNSTFRGDIALPLMLPLLKFLNGTNSYFFINLQPYFRWSRNPNHTTLDFALFQ
             . * *        *      .  *      . **   *       .  **

FIG. 2b
```

```
NPGLUC   APNVVV-QDGSLGYRNLFDAMSDAVYAALSRAGGGSIEIVVSESGWPSAGAFA-ATTN--
BEAN     SPNVVV-RDGQYGYQNLFDAMLDSVHAAIDNTRIGYVEVVSESGWPSDGGFG-ATYD--
PR-Q     SSEVVV-NDNGRGYRNLFDAILDATYSALEKASGSSLEIVVSESGWPSAGAGQLTSID--
BARLEY   PGTTVRDQNNGLTYTSLFDAMVDAVYAALEKAGAPAVKVVVSESGWPSAGGFA-ASAG--
At G62   GHSTYTDPQTGLVYRNLLDQMLDSVLFAMTKLGYPHMRLAISETGWPNFGDIDETGANIL
Bn A6    GNSTYTDPHTGLVYHNLVDQMLDSVIFAMTKLGYPYIRIAISETGWPNSGDIDEIGANVF
                  .   . *   *..  *..          .  **.***.  *         .

NPGLUC   NAATYYKNLIQHVKR-----GSPRRPNKVIETYLFAMFDENNKNPE-LEKHFGLFSPNKQP
BEAN     NARVYLDNLVRRAGR-----GSPRRPSKPTETYIFAMFDENQKSPE-IEKHFGLFKPSKEK
PR-Q     NARTYNNNLISHVKG-----GSPKRPSGPIETYVFALFDEDQKDPE-IEKHFGLFSANMQP
BARLEY   NARTYNQGLINHVGG-----GTPKKRE-ALETYIFAMFNENQKTGDATERSFGLFNPDKSP
At G62   NAATYNRNLIKKMSASPPIGTPSRPGLPIPTFVFSLFNENQKSGSGTQRHWGIFDPDGSP
Bn A6    NAATYNRNLIKKMTATPPIGTPARPGSPIPTFVFSLFNENKKPGSGTQRHWGILHPDGTP
         ** *   *      .           .   *   * **.*   .         *
```

FIG. 2c

```
NPGLUC    KYPLSFGFS--DRYWDISAENNATAASLISEM
BEAN      KYPFGFGAQRMQRLLLMSSMQHIPLRVTCKLEPSSQSLL
PR-Q      KYQISFN
BARLEY    AYNIQF
At G62    IYDVDFTGQTPLTGFNPLPKPTNNVPYKGQVWCVPVEGANETELEETLRMACAQSNTTCA
Bn A6     IYDIDFTGQKPLTGFNPLPKPTNNVPYKGQVWCVPVEGANETELEEALRMACARSNTTCA
              *                                           *

At G6     ALAPGRECYEPVSIYWHASYALNSYWAQFRNQSIQCFFNGLAHETTNPGNDRCKFP
Bn A6     ALVPGRECYEPVSVYWHASYALNSYWAQFRSQNVQCYFNGLAHETTNPGNDRCKFP

At G62    SVTL
Bn A6     SVTL
```

FIG. 2d

NPGLUC- Tobacco B 1,3-glucanase (Basic):-
De Loose M., Alliotte T., Gheysen G., Genetello C., Gielen J., Soetaert P., Van Montagu M. and Inz D. (1988) Gene 70, 13-23

BEAN - Bean B 1,3-glucanase:-
Edington, B.V., Lamb, C.J. and Dixon, R.A. (1991) Plant Mol. Biol. 16, 81-94

PR-Q - Tobacco B 1,3-glucanase (Extra-cellular):-
Payne, G., Ward, E., Gaffney, T., Ahl Goy, P., Moyer, M., Harper, A., Meins, F.Jr. and Ryals, J. (1990) Plant Mol. Biol. 15, 797-808.

BARLEY- Barley B 1,3-glucanase:-
Hoj, P.B., Hartman, D.J., Morrice, N.A., Doan, D.N.P. and Fincher, G.B. (1989) Plant Mol. Biol. 13, 31-42.

FIG. 2e

DNA sequence of the A.thaliana A6 gene together with the deduced primary structure of A6.

```
GAATTCACACAAAGCAATTAACAAAGTTAACCAAATCCCAAATTCGAATTTGGTTCCCTA
         10        20        30        40        50        60
TTCTACAGCCTAACCGTATTCTGAGATCTGTAACAGAGTCATGAACAGAAAATACCAACC
         70        80        90       100       110       120
TCGAGCTGACCGGAGCGGCACGATTTTGACTCGTCGAGCGTGTAAAGAAGGAAGTACCA
        130       140       150       160       170       180
TTGTTCCATTCAAGGTCGTAGGTAATACCACCGAGCTGCTCCTGGATGATATTGAAATTA
        190       200       210       220       230       240
```

FIG. 4a

| FIG. 4a |
|---|
| FIG. 4b |
| FIG. 4c |
| FIG. 4d |
| FIG. 4e |
| FIG. 4f |
| FIG. 4g |
| FIG. 4h |
| FIG. 4i |

FIG. 4

```
CGACCGTTGGTCCAGTCGTACCAAAGGTCGATCATCGAGAGATCGCCGGAGTAATTCATG
         250       260       270       280       290       300

AACATTAGCGGTGTGGAACTGGTGTGTGGCCATGGCGTCGGCACCGGCTCATCCGCGGGCA
         310       320       330       340       350       360

TTTTCACGCCGGCGGGTTATATAAAATGAAGATAACGATTACTATGAGTGGTCGTCTAAAAG
         370       380       390       400       410       420

CCATGTGTATCAGTGTGGTACTGAAGTTTTGGTTCGTGCACGGAAGATAAATTAAAATAC
         430       440       450       460       470       480

TATATAGTATACAGTTCTTTTAAATTCTACATAAATTGTTATCATCGAAACATACATTTT
         490       500       510       520       530       540
```

FIG. 4b

```
AGTCCATTAGTCTACTAAACTCATTATTGATGTATAATCTCTCAATCTACAATCAGAAAT
550       560       570       580       590       600

GTATTTGCAAAATTAACAATATTGGGGAAAGTGTTTCTTGGTTCAATTTGAACCGATCCA
610       620       630       640       650       660

ACCAACAATCCCTTTTAAAATCATAGCACAAAAGAACTATGAGAGTTTCAAAAGAAAATC
670       680       690       700       710       720

AAAAGCCAAAACAAAGCTTTTCTTGCATGACTCAATAAACCTACACTACACCATACTCTT
730       740       750       760       770       780

ACTTATAAACCCTTCATCTCCAATGCCACACCATTCCATCTTAAAATCACATTCTGATCATC
790       800       810       820       830       840
```

FIG. 4c

```
                                                                 M   S   L   L   A   F
ACCAACACATTGCAAACCAAACCAGACACAAAGACATGTCTCTTCTTGCTTTCT
         850       860       870       880       890       900

F   L   F   T   I   L   V   F   S   <-----
TCCTCTCTTCACCATCCTTGTCTTTTCAAGTAAGTCATCTTAATAATGCATCATGTTTACAT
         910       920       930       940       950       960

--------intron-------------                             ---->S   S   C   C
TTTCTTTTACGTAATCTCCCATATTGAACATGGTTTTCTTGGTTTTACAGGTTCATGTTGT
         970       980       990      1000      1010      1020

S   A   T   R   F   Q   G   H   R   Y   M   Q   R   K   T   M   L   D   L   A
TCCGCAACTCGGTTCCAAGGGCACAGGTACATGCAGAGGAAAACAATGCTAGATTTGGCT
        1030      1040      1050      1060      1070      1080

S   K   I   G   I   N   Y   G   R   R   G   N   N   L   P   S   P   Y   Q   S
AGCAAGATTGGTATCAACTATGGAAGAAGAGGAAACAACCTCCCATCTCCATATCAATCC
        1090      1100      1110      1120      1130      1140
```

FIG. 4d

```
I  N  F  I  K  S  I  K  A  G  H  V  K  L  Y  D  A  D  P  E
ATCAACTTCATCATCAAATCTATCAAAGCTGGTCATGTCAAGCTCTATGACGCCGATCCAGAG
         1150           1160           1170           1180           1190           1200

S  L  T  L  L  S  Q  T  N  L  Y  V  T  I  T  V  P  N  H  Q
AGTCTCACACTCCTCTCTCAAACCAATCTCTACGTCACCATAACCGTCCCTAACCACCAA
         1210           1220           1230           1240           1250           1260

I  T  A  L  S  S  N  Q  T  I  A  D  E  W  V  R  T  N  I  L
ATCACCGCCCTCAGCTCTAACCAAACCATAGCTGACGAATGGGTCAGAACTAACATCCTC
         1270           1280           1290           1300           1310           1320

P  Y  Y  P  Q  T  Q  I  R  F  V  L  V  G  N  E  I  L  S  Y
CCTTACTACTATCCACAAACACAAATCCGTTTTGTCCTTGTCGGAAACGAAATCCTCAGCTAC
         1330           1340           1350           1360           1370           1380

N  S  G  N  V  S  V  N  L  V  P  A  M  R  K  I  V  N  S  L
AATTCTGGGAATGTCTCTGTGAATCTTGTACCGGCGATGCGCAAGATCGTTAACTCACTC
         1390           1400           1410           1420           1430           1440
```

FIG. 4e

```
  R  L  H  G  I  H  N  I  K  V  G  T  P  L  A  M  D  S  L  R
AGATTACATGGGATTCACAACATCAAAGTTGGGACACCTCTAGCTATGGATTCTCCGG
            1450              1460              1470              1480              1490              1500

S  S  F  P  R  S  N  G  T  F  R  E  E  I  T  G  P  V  M  L
TCGTCGTTCCTCGATCGAACGGAACATTCCGGGAAGAAATCACCGGACCGGTGATGTTA
            1510              1520              1530              1540              1550              1560

P  L  L  K  F  L  N  G  T  N  S  Y  F  F  L  N  V  H  P  Y
CCGTTGCTGAAGTTTCTCAACGGAACAAACTCTTACTTCTTCCTTAATGTTCATCCTTAC
            1570              1580              1590              1600              1610              1620

F  R  W  S  R  N  P  M  N  T  S  L  D  F  A  L  F  Q  G  H
TTCCGTTGGTCAAGAAACCCCATGAACACCAGTTTGGATTTTGCTCTGTTCCAAGGACAC
            1630              1640              1650              1660              1670              1680
```

FIG. 4f

```
  S  T  Y  T  D  P  Q  T  G  L  V  Y  R  N  L  L  D  Q  M  L
TCAACCTATACCGATCCTCAAACCCGGTTTGGTTTACCGTAATCTTCTAGACCAAATGTTG
        1690         1700        1710        1720        1730        1740

D  S  V  L  F  A  M  T  K  L  G  Y  P  H  M  R  L  A  I  S
GATTCGGTTCTCTTCGCCATGACCAAACTCGGTTATCCACATATGCGCCTCGCGATCTCT
        1750        1760        1770        1780        1790        1800

E  T  G  W  P  N  F  G  D  I  D  E  T  G  A  N  I  L  N  A
GAAACCGGATGGCCTAATTTCGGTGACATCGACGAGACCGGAGCCAACATTCTCAACGCA
        1810        1820        1830        1840        1850        1860

A  T  Y  N  R  N  L  I  K  K  M  S  A  S  P  P  I  G  T  P
GCTACCTATAACCGTAATCTGATCAAGAAGATGAGCGCAAGTCCTCCAATCGGTACACCA
        1870        1880        1890        1900        1910        1920

S  R  P  G  L  P  I  P  T  F  V  F  S  L  F  N  E  N  Q  K
TCAAGACCCGGTTTACCGATACCGACATTGTTTTCTCCTTATTCAACGAAAACCAGAAA
        1930        1940        1950        1960        1970        1980

S  G  S  G  T  Q  R  H  W  G  I  F  D  P  D  G  S  P  I  Y
TCCGGTTCGGGGACACAGAGACATTGGGAATCTTCGATCCCGACGGTTCACCAATCTAC
        1990        2000        2010        2020        2030        2040
```

FIG. 4g

```
  D   V   D   F   T   G   Q   T   P   L   T   G   F   N   P   L   P   K   P   T
GACGTAGAGATTTCACCGGTCAAACACCCTTAACCGGTTTCAACCGGTTTCAACCGTTACCTAAACCGACG
            2050                2060                2070                2080                2090                2100

N   N   V   P   Y   K   G   Q   V   W   C   V   P   V   E   G   A   N   E   T
AACAACGTTCCTTACAAAGGTCAAGTGTGGTGCGTACCAGTCGAAGGAGCCAACGAGACT
            2110                2120                2130                2140                2150                2160

E   L   E   E   T   L   R   M   A   C   A   Q   S   N   T   T   C   A   A   L
GAGCTTGAAGAAACATTGAGGATGGCTTGTGTGCCCAAAGCAACACCACTTGTGCAGCTTTA
            2170                2180                2190                2200                2210                2220

A   P   G   R   E   C   Y   E   P   V   S   I   Y   W   H   A   S   Y   A   L
GCTCCTGGGAGAGAATGTTACGAACCAGTCTCCATTTATTGGCATGCAAGCTACGCGCTT
            2230                2240                2250                2260                2270                2280

N   S   Y   W   A   Q   F   R   N   Q   S   I   Q   C   F   F   N   G   L   A
AATTCGTACTGGGCTCAGTTTCGTAACCAAAGCATTCAATGTTTCTTCAATGGATTGGCT
            2290                2300                2310                2320                2330                2340
```

FIG. 4h

```
  H  E  T  T  N  P  <------------intron------------
CATGAGACAACAACCAACCCTGGTGAGCCATTCTTTGTAGTTCCAAATTAGACCAAAA
     2350           2360          2370          2380          2390          2400

------------------->G  N  D  R  C  K  F
TAACCTTTTCGTATAGTCACTAACAAAGATTTTTACAGGAAATGATCGTTGCAAGTTTC
     2410          2420          2430          2440          2450          2460

P  S  V  T  L  *
CGAGCGTTACTCTGTGAGGAGGACTTGAGGAAGAAGACACATGATTAAAGCTGGATTATT
     2470          2480          2490          2500          2510          2520

CGTATAACTCAATAAATGTTCCTTATCTTTTTTTTTATTATATACCTTTTTT
     2530          2540          2550          2560
```

FIG. 4i

Alignment of the DNA sequences of the *A.thaliana* A6 gene and the *B.napus* A6 cDNA.

```
At   862  CCAGACACAAACACAAAGACATGTCTCTTCTTCCTCTTCACC  911
              |||||||||||||||||||||
Bn     1  .........................CTTTCTTCCTCTTCACC   17

At   912  ATCCTTGTCTTTTCAAGTAAGTCATCTTAATAATGCATCATGTTTACATT  961
          || |  ||||||||||
Bn    18  CTCGTCGTCTTTCAA...................................   40

At   962  TTCTTTACGTAATCTCCCATATTGAACATGGTTTTCTTGGTTTTACAGGT 1011
                                                        ||    ||
Bn    35  ..............................................GT     35

At  1012  TCATGTTGTTCCGCAACTCGGTTCCAA...GGGCACAGGTACATGCAGAG 1058
          ||||| || ||  ||||||||| |||||      |||||||||||| ||||
Bn    36  ACAAGTTGCTCAGCGGTTGGGTTCCAACATCCGCACAGGTATATACAGAA   85
```

| FIG. 5a-1 |
| FIG. 5a-2 |
| FIG. 5a-3 |
| FIG. 5a-4 |
| FIG. 5a-5 |
| FIG. 5a-6 |
| FIG. 5a-7 |
| FIG. 5a-8 |

```
1059  GAAAACAATGCTAGAGATTTGGCTAGCAAGATTGGTATCAACTATGGAAGAA  1108
      ||||| |||||||||||| ||||||| ||||||| |||||||||||||||||
  86  AAAAACGATGCTAGAGTTAGCCAGCAAGATTGGTATTAACTATGGTAGAC    135

1109  GAGGAAACAACCTCCCATCTCCATATCAATCCATCAACTTCATCAAATCT   1158
      ||||||||||||| ||||||||| ||||| |||||||||||||||| |||
 136  AAGGAAACAACCTACCATCTCCCTTACCAATCGATCAATTCATCAAACTC   185

1159  ATCAAAGCTGGTCATGTCAAGCTCTATGACGCCGATCCAGAGAGTCTCAC   1208
      ||||||||||||||||||||||||||| |||||||||||||||||||||
 186  ATCAAAGCCGGTCATGTCAAGCTCTACGACGCCGATCCAGAGAGTCTAAC   235

1209  ACTCCTCTCTCAAACCAATCTCTACGTCACCATAACCGTCCCTAACCACC   1258
      |||||||||||||||||||||||||||||||||| |||| ||||||||||
 236  ACTCCTCTCTCAAACCAATCTCTACGTCACCATAGCGGTGCCAACCCACC   285

1259  AAATCACCGCCCTCAGCTCTAACCAAACCATAGCTGACGAATGGGTCAGA   1308
      ||||||||||||||||||||| ||||||||||||||||||||||||||||
```

FIG. 5a-2

```
 286 AGATCACTTCCCCTCAGCGCCAAACCAAACTACAGCTGAAGATTGGGTCAAA  335
         |||||||||||||||||||||||||||||||||||||||||||||||||||
1309 ACTAACACATCCTCCCCTTACTATCCACAAAACACAAATCCGTTTTGTCCTTGT 1358
     ||   ||   |||||||||| |  |||||||||| |  ||||||||||||||
 336 ACCAATATCCTCCCTTACTACCACACAAATACGATTTGTCCTTGT 385

1359 CGGAAACGAAATCCTCAGCTACAATTCTGGGAATGTCTCTGTGAATCTTG 1408
     ||||| ||||||||||||| |   ||  ||  |||  |||||  |||
 386 TGGAAACGAAATCCTCTCCGTCAAAGATAGGAACATAACCGGCAATGTCG 435

1409 TACCGGCGATGCGCAAGATCGTTAACTCACTCAGATTACATGGGATTCAC 1458
     |||||||| |||| |||| ||| ||  |||||||||||||| ||||||||
 436 TACCGGCAATGCGAAAAATCGTGAACTCTCTCAGAGCCCATGGGATTCAC 485

1459 AACATCAAAGTTGGGACACCCTCTAGCTATGGATTCTCTCCGGTCGTCGTT 1508
     |||||||||||| |||||||| |||||||||||||||||  ||| || ||
 486 AACATCAAAGTCGGGTACACCTTTAGCTATGGATTCTCTTGATCAACGTT 535
```

FIG. 5a-3

```
1509  TCCTCGATCGAACGGAACATTCCGGGAAGAAATCACCGGACCGGTGATGT 1558
           ||| |||||   |||||||||||| ||| ||| ||||   |||| ||||
 536  TCCGCCGTCGAACTCAACATTCCGGGGAGATATCGCCTTACCGTTAATGT 585

1559  TACCGTTGCTGAAGTTTCTCAAGCGGAACAAACTCTTACTTCTTCCTTAAT 1608
      | ||||||||||||||||||||| ||||||||||||||||||||| |||
 586  TGCCGTTGCTGAAGTTTCTCAACGGAACAAACTCTTACTTCTTTATCAAT 635

1609  GTTCATCCTTACTTCCGTTGGTCAAGAAACCCCATGAACACCAGTTTGGA 1658
      ||||  |||||||||||||||||||||||| |||| |||||||||||||
 636  CTTCAACCTTACTTCCGTTGGTCAAGAAACCCTAATCACACCAGTTGGA 685

1659  TTTTGCTCTGTTCCAAGGACACTCAACCTATACCGATCCTCAAACCGGTT 1708
      |||  ||||||||||||| |||||||| ||||||||||||| |||||||
 686  TTTCGCTCTGTTTCAAGGAAAACTCAACTTATACCGATCCTCATACCGGTT 735

1709  TGGTTTACCGTAATCTTCTAGACCAAATGTTGGATTCGGTTCTCTTCGCC 1758
      |||||||||| ||||||| |||||||||||||||||||||| ||||||
 736  TGGTTTACCATAATCTTGTAGACCAAATGTTGGATTCGGTTATCTTCGCC 785
```

FIG. 5a-4

```
1759 ATGACCAAACTCGGTTATCCACATATGCGCCTCGGCGATCTCTGAAACCGG 1808
     ||||||| |||||||| |||||| |||  ||| |||  |||||||||||||
 786 ATGACCAAGCTCGGTTATCCATACATCCGTATCCGCAATCTCTGAAACCGG  835

1809 ATGGCCTAATTTCGGTGACATCGACGAAACCGGAGCCAACATTCTCAACG  1858
     |||||||| | ||| ||||||||||||||||||||||| |||| |||||
 836 ATGGCCTAACTCCCGGCGACATCGACGAAATCGGAGCTAACGTTTTCAACG  885

1859 CAGCTACCTATAACCGTAATCTGATCAAGAAGATGAGCCGCAAGTCCTCCA  1908
       ||| |||||||||  ||| |||||||||||||||||| ||| ||| ||
 886 CCGCCACGTATAACCGGAATTTGATCAAGAAGATGACCGCAACTCCACCA   935

1909 ATCGGTACACCATCAAGACCCGGTTTACCAATACCGACATTGTTTTCTC   1958
     ||||||||||| |||| ||||||||  |||| |||||||||||||||||
 936 ATCGGTACACCAGCTAGACCCGGTTCACCTATACCGACATTGTTTTCTC    985

1959 CTTATTCAACGAAAACCAGAAATCCGGTTCGGGGACACAGAGACATTGGG  2008
     ||||||| |||||| ||||||  |||||||||||||| ||||||||||||
 986 CTTATTTAACGAAAACAAGAAACCCGGTTCGGGAACACAAAGACATTGGG  1035
```

FIG. 5a-5

```
2009  GAATCTTCGATCCCGACGGTTCACCAATCTACGACGTAGATTTCACCGGT  2058
      ||||||  ||| |||| ||||||||||||| ||||||||| ||| |||||
1036  GAATCTTGCATCCGACGGTACACCAATCTACGACATTGATTTTACCGGT   1085

2059  CAAACACCCCTTAACCGGTTTCAACCCGTTACCTAAACCGACGAACAACGT 2108
      |||  |||| |||||||||||| ||||| ||| ||||||||| |||||||
1086  CAAAAACCCCTTAACCCTCTGCCTAAACCGACGAATAACGT           1135

2109  TCCTTACAAGGTCAAGTGTGGTGCGTACCAGTCGAAGGAGCCAACGAGA   2158
      |||||||||||||||| ||||||||||||||| |||||||||||||||||
1136  TCCTTACAAGGTCAAGTGTGGTGCGTACCGGTCGAAGGAGCCAACGAGA   1185

2159  CTGAGCTTGAAGAAACATTGAGGATGGCTTGTGCCCAAAGCAACACCACT  2208
      ||||||| ||| ||  || ||||||||||||||||| |||||||||| |
2186  CTGAGCTCGAGGAAGCTTTGAGGATGGCTTGTGCCCGAAGCAACACGACG 1235
```

FIG. 5a-6

```
2209 TGTGCAGCTTTAGCTCCTGGGAGAGAATGTTACGAACCAGTCTCCATTTA 2258
     ||||| ||||| |  ||||| |||||||||||||||||||| ||| |||
1236 TGTGCGGCTTTGGTTCCTGGCAGAGAATGTTACGAGCCGGTCTCTGTTTA 1285

2259 TTGGCATGCAAGCTACGCGCTTAATTCGTACTGGGCTCAGTTTCGTAACC 2308
     ||||| ||||||||| ||||||| ||||||||||||||| ||||| |||
1286 TTGGCACGCAAGCTACGCGCTTAACTCGTACTGGGCACAGTTCCGTAGCC 1335

2309 AAAGCATTCAATGTTTCTTCAATGGATTGGCTCATGAGACAACAACCAAC 2358
     ||| ||  ||||||| ||| ||||||||| |||||||||||| ||  ||
1336 AAAACGTCCAATGTTACTTCAATGGATTAGCTCATGAGACCACGACTAAC 1385
```

FIG. 5a-7

```
2359 CCTGGTGAGCCATTCTTTGTAGTTCCAAATTTAGACCAAAATAACCTTT 2408
         ||||                              ||||
1386 CCTG..............................CCTG

2409 TCGTATAGTCACTAACAAAGATTTTTTACAGGAAATGATCGTTGCAAGTT 2458
                                ||||||||||||||||||||||||
                       .........GAAATGATCGCTGCAAGTT 1408

2459 TCCGAGCCGTTACTCTCTGTGAGGAGGACTTGAGGAAGAAGACACATGATTAA 2508
     ||||||||||||||||||||||||||  ||   |||   |||
2459 TCCGAGCCGTTACTCTCTGTGAGGAAGAACGCCTGAAAGAGATTAAGATGAT 1458

2509 AGCTGGATTATTCGTATAACTCAATAATGTTCCTTATCTTTTTTTTTATT 2558
      |||   |||  ||||
1459 CAAAGCTGGATTATTCGTATTACTC 1484

2559 ATACCTTTTT 2569
```

FIG. 5a-8

Alignment of the putative polypeptides encoded by the *A.thaliana* A6 gene and the *B.napus* cDNA A6.

Percent Similarity: 90    Percent Identity: 83

```
At   1 MSLLAFFLFTILVFSSSCCSATRFQ.GHRYMQRKTMLDLASKIGINYGRR    49
         ||||::||||.:||| .|||. .:||.:|:|||||||:||||||||||:
Bn   1 .....FFLFTLVVFSSTSCSAVGFQHPHRYIQKKTMLELASKIGINYGRQ    45

At  50 GNNLPSPYQSINFIKSIKAGHVKLYDADPESLTLLSQTNLYVTITVPNHQ    99
       |||||||||||||| ||||||||||||||||||||||||||||:|.|:|
Bn  46 GNNLPSPYQSINFIKLIKAGHVKLYDADPESLTLLSQTNLYVTIAVPTHQ    95
```

FIG. 5b-1

| FIG. 5b-1 |
|-----------|
| FIG. 5b-2 |
| FIG. 5b-3 |

FIG. 5b

```
100 ITALSSNQTIADEWVRTNILPYYPQTQIRFVLVGNEILSYNSGNVSVNLV 149
    ||.||.|||.|.::||:|||||||||||||||||||   ..  |:..|:|
 96 ITSLSANQTTAEDWVKTNILPYYPQTQIRFVLVGNEILSVKDRNITGNVV 145

150 PAMRKIVNSLRLHGIHNIKVGTPLAMDSLRSSFPRSNGTFREEITGPVML 199
    ||||||||||| ||||||||||||||||||.|:.||::|. |:||  .|
146 PAMRKIVNSLRAHGIHNIKVGTPLAMDSLRSTFPSNSTFRGDIALPLML 195

200 PLLKFLNGTNSYFFLNVHPYFRWSRNPMNTSLDFALFQGHSTYTDPQTGL 249
    |||||||||||||| ||:||||||||||:|:.:|||||||||||||||
196 PLLKFLNGTNSYFFINLQPYFRWSRNPNHTTLDFALFQGNSTYTDPHTGL 245

250 VYRNLLDQMLDSVLFAMTKLGYPHMRLAISETGWPNFGDIDETGANILNA 299
    ||:|||||||||||:|||||||||||:|||||||||||||||||||:||
246 VYHNLVDQMLDSVIFAMTKLGYPYIRIAISETGWPNSGDIDEIGANVFNA 295
```

FIG. 5b-2

```
300 ATYNRNLIKKMSASPPIGTPSRPGLPIPTFVFSLFNENQKSGSGTQRHWG 349
    ||||||||||||.|.|||.|.|||||||||||||||.|.||||||||||
296 ATYNRNLIKKMTATPPIGTPARPGSPIPTFVFSLFNENKKPGSGTQRHWG 345

350 IFDPDGSPIYDVDFTGQTPLTGFNPLPKPTNNVPYKGQVWCVPVEGANET 399
    |:.||.||||||.||||.||||||||||||||||||||||||||||||
346 ILHPDGTPIYDIDFTGQKPLTGFNPLPKPTNNVPYKGQVWCVPVEGANET 395

400 ELEETLRMACAQSNTTCAALAPGRECYEPVSIYWHASYALNSYWAQFRNQ 449
    ||||.||||||:|||||||.||||||||||:|||||||||||||||.|
396 ELEEALRMACARSNTTCAALVPGRECYEPVSVYWHASYALNSYWAQFRSQ 445

450 SIQCFFNGLAHETTTNPGNDRCKFPSVTL 479
    .:|::|||||||||||||||||||||||
446 NVQCYFNGLAHETTTNPGNDRCKFPSVTL 474
```

FIG. 5b-3

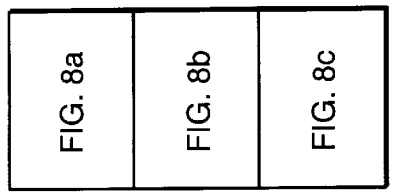
a) Fusion of the A9 promoter to the A.thaliana callase gene
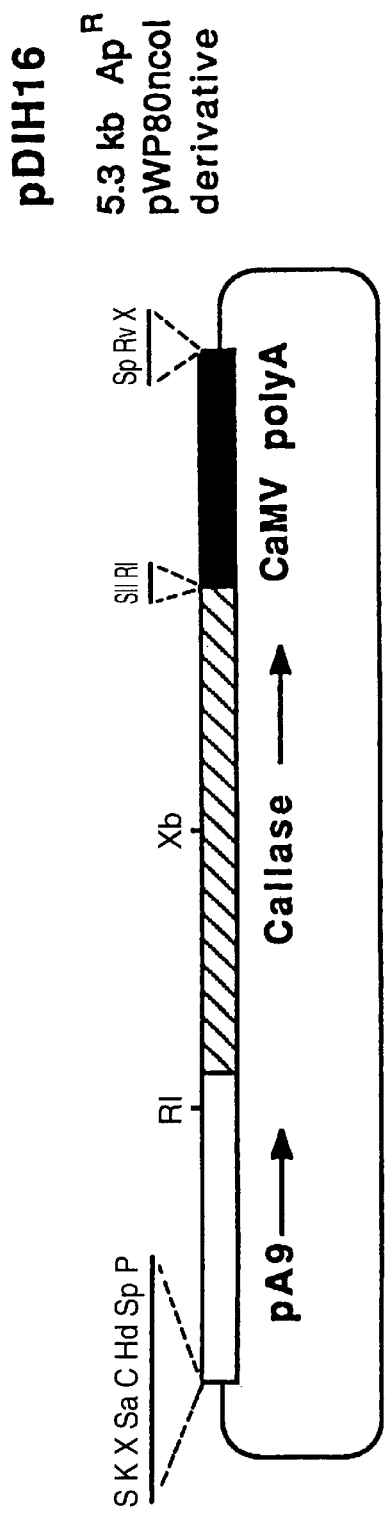
FIG. 8a

CALLASE-RELATED DNAS AND THEIR USE IN ARTIFICIAL MALE STERILITY

BACKGROUND OF THE INVENTION

This invention relates to recombinant, isolated and other synthetic DNA useful in male-sterility systems for plants. In particular, the invention relates to restorable male-sterility systems. Male-sterile plants are useful for the production of hybrid plants by sexual hybridisation.

Hybrid plants have the advantages of higher yield and better disease resistance than their parents, because of heterosis or hybrid vigour. Crop uniformity is another advantage of hybrid plants when the parents are extensively homozygous; this leads to improved crop management. Hybrid seed is therefore commercially important and sells at a premium price.

Producing a hybrid plant entails ensuring that the female parent does not self-fertilise. There have been many prior proposals, mechanical, chemical and genetic, for preventing self-pollination. Among the genetic methods is the use of anther-specific genes or their promoters to disrupt the normal production of pollen grains. An anther-specific promoter, for example, can be used to drive a "male-sterility DNA" at the appropriate time and in the right place. Male sterility DNAs include those coding for lytic enzymes, including those that lyse proteins, nucleic acids and carbohydrates. Glucanases are enzymes which break down carbohydrates.

In EP-A-0344029 (Plant Genetic Systems (PGS)) and WO-A-9211379 (Nickerson International Seed Company Limited) glucanase-coding DNA features among possible malesterility DNAs. Although many plant glucanases have been characterised and the genes cloned in some cases (eg defence-related "PR" glucanases), to date no glucanase with properties consistent with a role in microspore release has been reported. Microspore release is the process by which the immature microspores are liberated from a protective coat of β(1,3) poly-glucan (callose) laid down by the microsporogenous cells before meiosis (Rowley, *Grana Palynol.*, 2, 3–31 (1959); and Heslop-Harrison, *Can. J. Bot.* 46, 1185–1191(1968) and *New Phytol.*, 67, 779–786 (1968)). The anther-expressed glucanase responsible for the dissolution of this callose coat is known as callase. Callase is synthesised by the cells of the tapetum and secreted into the locule. The appearance of the enzyme activity is developmentally regulated to coincide precisely with a specific stage of microspore development.

The basis of the use of a glucanase as a sterility DNA lies in the fact that mis-timing of the appearance of callase activity is associated with certain types of male-sterility (Warmke and Overman, *J. Hered.* 63 103–108 (1972)). Two types are recognised depending on whether the appearance of glucanase activity is premature or late. Since both types are found in nature, one important attraction of glucanase as a potential sterility DNA is that it already occurs in a natural system. Although plants that fail to produce active callase have not been described in nature, mutants of this type almost certainly occur. Failure to produce callase would prevent microspore-release, thereby causing pollen abortion and male-sterility. So, preventing callase expression would form the basis of a male-sterility system.

Several studies suggest that callase is probably different from other types of glucanases, such as the "PR" glucanases. For example, callase activity may be subject to both transcriptional and post-transcriptional control. This is suggested by the fact that there is a strong relationship between locule pH, callase activity, and the timing of microspore release (Izhar and Frankel, *Theor. and Appl. Genet.* 41, 104–108 (1971)). Locule pH and callase activity change coordinately in a developmentally regulated manner. In fertile *Petunia hybrida* anthers, the pH during meiosis is 6.8–7.0 and callase activity is undetectable. Following meiosis, at the tetrad stage, the locule pH drops in a precipitous fashion to 5.9–6.2 and callase activity increases sharply resulting in microspore release.

In certain male-sterile Petunia strains, the drop in pH and the appearance of callase activity are precocious and apparently result in the breakdown of microsporogenesis. Similarly, in another class of mutants, the drop in locule pH and the appearance of callase activity are both late and apparently result in the abortion of the microspores.

Thus, it appears that:
(1) the timing of the appearance of callase activity is critical for normal microspore development. (Presumably the abortion of prematurely released microspores indicates that they must reach a certain developmental stage before becoming capable of surviving without the protection of the callose coat);
(2) the decrease in locule pH parallels the appearance of callase activity; and
(3) the two events (production of callase activity and pH drop) are coordinately regulated in some manner.

The exact nature of the co-ordinate regulation of callase activity and pH is not known. The drop in pH may activate an otherwise fully functional enzyme (passive activation). Alternatively, the enzyme may be synthesised in an inactive form, rather like the zymogen of a protease, and activated as a consequence of some pH-dependent event such as the removal of an N-terminal or C-terminal addition (positive activation). The fact that callase, and possibly all glucanases, including PR-glucanases, has no detectable activity above pH 6.3, well below that encountered in the anther before microspore release may favour a passive activation theory.

However, since current assays for callase are crude and rely on the measurement of activity, it is impossible to say whether the enzyme is: i) produced before microspore release, but in a non-functional form for later activation; ii) synthesised in an active form but only at the precise time it is required; or iii) synthesised in advance in an active form, stored within the tapetal cells in some kind of vesicle, and released into the locule at microspore-release. The fact that pH drop and callase activity are so consistently correlated, even in cases where callase activity is found well before the normal time of microspore release, might indicate that the enzyme is synthesised in an inactive form in advance of its requirement and that the pH drop is in some way responsible for its activation. The alternative is that the drop in pH triggers the synthesis of callase in the tapetal cells. The important point is that, without knowing which is correct, it is impossible to predict whether the expression of glucanases that are not callase will produce male sterility.

The fact that callase appears different in certain respects from previously characterised glucanases has three important consequences:
(1) glucanases, such as defence-related "PR" glucanases may not function efficiently under the conditions within the locule and may therefore not prove sufficiently useful as components of male sterility DNAs;
(2) in the event that such glucanases are active within the locule, maximum naturalness, in terms of mimicking existing types of male-sterile plants, would nevertheless demand the use of the authentic callase gene. In this respect a male sterility system based on the use of a callase gene would be superior to any previously described system; and (3) systems based on preventing callase expression by destroying the callase mRNA using anti-callase mRNA, ribozymes or a callase anti-sense RNA require detailed knowledge of the nucleotide sequence of the callase mRNA.

SUMMARY OF THE INVENTION

The present invention is based on the discovery and identification of a callase gene in members of the family Brassicaceae. A cDNA derived from this gene in *Brassica napus* and a genomic version of the gene from *Arabidopsis thaliana* have been cloned. These and related DNAs (including the promoter of the callase gene) can be used in the construction of artificial male-sterility systems. Fertility can be restored in the F1 generation using antisense RNA, ribozymes and RNA-binding proteins.

According to a first aspect of the present invention, there is provided a recombinant or isolated DNA encoding an enzyme which has the activity of a callase enzyme particularly a 53 kDa callase enzyme of *Brassica napus* or an equivalent protein in another member of the family Brassicaceae.

In this specification, the gene encoding the 53 kDa callase enzyme of *B. napus* and equivalents of that gene in other members of the family Brassicaceae will be referred to as the A6 gene.

Preferred embodiments of this aspect of the invention include the gene encoding the 53 kDa callase enzyme from *B. napus* itself and the equivalent enzyme from *Arabidopsis thaliana* and their cDNAs.

The molecular weights quoted above are putative and derived from the number of amino acids believed to be present, as deduced from the DNA sequence. The 53 kDa protein encoded by the A6 gene of *B. napus* has 474 amino acids. It will therefore be appreciated that the molecular weights refer to the un-glycosylated protein. In addition, the effect on any other post-translational processing such as partial proteolysis is discounted.

Although the figure given above relate only to proteins of *B. napus*, those skilled in the art will readily be able to identify equivalent proteins from other members of the family Brassicaceae. For example, the equivalent A6 gene in *A. thaliana* encodes a putative protein of 479 amino acids in length having a calculated molecular weight of 53.7 kDa. Such equivalent genes may be identified by hybridisation studies, restriction fragment length polymorphism (RFLP) and other methods known in the art. Genes or other DNA sequences, whether natural, engineered or synthetic, encoding closely equivalent proteins may for example hybridise under stringent conditions (such as at approximately 35° C. to 65° C. in a salt solution of approximately 0.9 molar) to the *B. napus* A6 gene, or fragments of it of, for example, 10, 20, 50 or 100 nucleotides. A 15–20 nucleotide probe would be appropriate under many circumstances.

DNA sequences modified or differing from natural Brassicaceae A6 sequences are within the scope of the invention if, for example, they satisfy the above hybridisation criteria, or would do so but for the degeneracy of the genetic code.

The preferred A6 coding sequence described in this specification is from *Brassica napus* or *Arabidopsis thaliana* and can be isolated by methods known in the art, for example by (a) synthesising cDNA from mRNA isolated from the stamens of *B. napus* or *A. thaliana*, (b) isolating this cDNA, (c) using this cDNA as a probe to identify regions of the plant genome of a chosen member of the family Brassicaceae that encode stamen-specific mRNA and (d) identifying the upstream (5') regulatory regions that contain the promoter of this DNA. This procedure also demonstrates that probes based on, or derived from, the coding regions of a stamen-specific DNA from one species of plant may be used to isolate DNA sequences encoding stamen-specific mRNAs from other species.

Particularly preferred coding sequences are shown in FIG. 1 (for the *B. napus* A6 gene) and FIG. 4 (for the *A. thaliana* A6 gene) as will subsequently be described in the examples. Those skilled in the art will, with the information given in this specification, be able to identify with sufficient precision the coding regions and to isolate and/or recombine DNA containing them.

DNA in accordance with the first aspect of the invention is useful in the provision of male sterility systems. By operatively linking the DNA with a suitable promoter, it can be expressed at a time that would naturally be inappropriate, for example too early. Suitable promoters include tapetum-specific promoters other than the natural A6 promoter. Among the preferred promoters are those described and claimed in U.S. Ser. No. 08/417,460, now allowed U.S. Pat. No. 5,723,754, and designated A3 and A9. In U.S. Ser. No. 08/417,460, now allowed U.S. Pat. No. 5,723,754, the gene encoding the 12.9 kDa protein in *A. thaliana* and equivalents of that gene in other members of the family Brassicaceae are referred to as the A3 gene; the gene encoding the 11.6 kDa protein in *A. thaliana* and equivalents of that gene in other members of the family Brassicaceae, including the gene encoding a 10.3 kDa protein in *B. napus,* are referred to as the A9 gene. The contents of U.S. Ser. No. 08/417,460, now allowed U.S. Pat. No. 5,723,754, are hereby incorporated by reference.

The discovery underlying the present invention can be harnessed in a number of other ways to provide a male-sterility system. The A6 promoter can for example be used to drive male-sterility DNA, which does not need to be specific.

According to a second aspect of the invention, there is provided a recombinant or isolated DNA sequence comprising a promoter which naturally drives the expression of a callase enzyme, particularly a 53 kDa callase enzyme of *Brassica napus* or an equivalent protein in another member of the family Brassicaceae.

Because of the natural specificity of the regulation of expression of the A6 gene, it is not necessary for the A6 promoter to be linked to specific disrupter DNA to provide a useful male-sterility system (although it can be); non-specific disrupter DNA can be used.

A6 promoters from other members of the family Brassicaceae and modified A6 promoters can be used, and if necessary located or identified and isolated as described above for the A6 coding sequences, *mutatis mutandis*. Again, preferred promoters are from *B. napus* and *A. thaliana* and used naturally to drive the coding sequences shown in FIGS. 1 and 4, which will be described later.

A6 promoter-containing DNA in accordance with the invention can, as indicated above, be used to confer male sterility on plants, particularly those belonging to the family Brassicaceae, in a variety of ways as will be discussed below. In an important embodiment of the invention, therefore, a promoter as described above is operatively linked to DNA which, when expressed, causes male sterility.

Since an effective sterility system is complete, propagation of the seed parent must proceed either by asexual means or via the pollination of the male-sterile by an isogenic male-fertile line, and the subsequent identification or selection of male sterile plants among the offspring. Where vegetative propagation is practical, the present invention forms a complete system for hybrid production. Where fertility restoration is necessary to produce a seed crop, the present invention forms the basis of a new male sterility system. In some seed crops where the level of cross pollination is high, seed mixtures may enable restoration to be bypassed. The male sterility will be particularly useful in crops where restoration of fertility is not required, such as in the vegetable Brassica spp., and such other edible plants as lettuce, spinach, and onions.

DNA in accordance with the invention and incorporating the A6 promoter can drive male sterility DNA thereby producing male sterile plants, which can be used in hybrid production. The promoters are highly tapetum-specific and so the sterility DNA is only expressed in the tapetum. The control of expression is very strong and the DNA is not expressed in other cells of the plant. The system prevents the production of viable pollen grains. All transformed plants and their progeny are male sterile; there is no problem with meiotic segregation.

A construct comprising a promoter operatively linked to a male sterility DNA can be transformed into plants (particularly those of the genus Brassica, but also other genera such as Nicotiana and Hordeum) by methods which may be well known in themselves. This transformation results in the production of plants, the cells of which contain a foreign chimeric DNA sequence composed of the promoter and a male sterility DNA. Male-sterility DNA encodes an RNA, protein or polypeptide which, when produced or over-produced in a stamen cell of the plant, prevents the normal development of the stamen cell. The A6 promoter may be used to drive a variety of male sterility DNA sequences which code for RNAs, proteins or polypeptides which bring about the failure of mechanisms to produce viable male gametes. The invention is not limited by the sequence driven, but a number of classes and particular examples of male sterility promoter-drivable sequences are preferred.

For example, the drivable male sterility DNA may encode a lytic enzyme. The lytic enzyme may cause degradation of one or more biologically important molecules, such as macromolecules including nucleic acid, protein (or glycoprotein), carbohydrate and (in some circumstances) lipid.

Ribonuclease (such as RNase T1 and barnase) are examples of enzymes which cause lysis of RNA. Examples of enzymes which lyse DNA include exonucleases and endonucleases, whether site-specific such as EcoRI or non-site-specific.

Glucanases other than the callase to whose coding sequence a promoter of the invention is naturally linked represent examples of enzymes which cause lysis of a carbohydrate. The enzyme glucanase (callase) is naturally produced in anthers where it functions to release the young microspores from a protective coat of poly-glucan laid down before meiosis. The appearance of the enzyme activity is developmentally regulated to coincide with the correct stage of microspore development. One important attraction of glucanase as a potential sterility DNA is that plants are found in nature that are male-sterile due to mutations causing mistiming of callase expression and the destruction of the microspores. Two types are recognised depending on whether the appearance of callase activity is premature or late. The expression of many genes, including those expressed within the anther, exhibit various patterns of temporal regulation. Therefore, in order to use callase as a sterility DNA, the promoter chosen to drive expression of the gene must provide an appropriate developmental regulation of glucanase activity, preferably by mimicking the pattern of expression found in association with natural male-sterility. One means of achieving male sterility is to isolate the promoter from a tapetum-specific gene with the same pattern of expression as found for glucanase activity in male-sterile mutant plants. Since late expression of a glucanase is unlikely to produce sterility in plants with a functional anther glucanase gene, the sterility factor would require a promoter capable of driving transcription before the appearance of normal glucanase activity. In the RM cms mutant of Petunia (Izhar, S. and Frankel, R. *Theor. Appl. Genet.*, 41 104–108 (1971)) callase expression within the anther first appears at the end of meiotic prophase, and increases to a maximum by the completion of meiosis. This pattern of expression contrasts with that in normal Petunia plants, where glucanase activity within the anthers appears concomitantly with the breakdown of the tetrads and the release of the young microspores. The aberrant pattern of callase activity found in the cms mutant is thought to be responsible for the destruction of the microspores and male sterility. Thus, to mimic this mutation using a sterility DNA encoding a glucanase enzyme requires a promoter capable of driving transcription of the male sterility DNA within the anthers, and preferably within the tapetum, during the phase of anther development between prophase of meiosis and the appearance of the tetrad of microspores; the A3 and A9 promoters discussed above are therefore well suited to drive this gene. A tapetum-specific (or at least anther-specific) promoter is also advantageous since $\beta(1,3)$-glucans are found elsewhere within plants, for example in phloem sieve elements, where they presumably perform essential functions.

The spatial regulation of the enzyme should also ensure access to the target cells. Secretion into the locular space is ensured by the provision in a preferred embodiment, of the natural or any other suitable signal sequence in a translational fusion with the glucanase coding sequence.

DNA encoding glucanase is advantageous as male sterility DNA, as it has no product which is cytotoxic outside the target cell. Glucanase as a male sterility DNA mimics natural systems and is inherently less destructive than for example ribonuclease, and so does not present such a problem if 'leakage' occurs into other cells.

Actinidin is an example of a protease, DNA coding for which can be suitable male sterility DNA. Other examples include papain zymogen and papain active protein.

Lipases whose corresponding nucleic acids may be useful as male sterility DNAs include phospholipase $A_2$.

Male sterility DNA does not have to encode a lytic enzyme. Other examples of male sterility DNA encode enzymes which catalyse the synthesis of phytohormones, such as isopentyl transferase, which is involved in cytokinin synthesis, and one or more of the enzymes involved in the synthesis of auxin. DNA coding for a lipoxygenase or other enzymes having a deleterious effect may also be used.

Other male sterility DNAs include antisense sequences. Introducing the coding region of a gene in the reverse orientation to that found in nature can result in the down-regulation of the gene and hence the production of less or none of the gene product. The RNA transcribed from antisense DNA is capable of binding to, and destroying the function of, a sense RNA version of the sequence normally found in the cell thereby disrupting function. Examples of such anti-sense DNAs are the antisense DNAs of the A6 gene produced in the anther under control of the A6 promoter. Since this gene is normally expressed in the tapetum, antisense to it may be expected to disrupt tapetal function and result in male sterility.

It is not crucial for antisense DNA solely to be transcribed at the time when the natural sense transcription product is being produced. Antisense RNA will in general only bind when its sense complementary strand, and so will only have its toxic effect when the sense RNA is transcribed. Antisense DNA corresponding to some or all of the DNA encoding the A6 gene product may therefore be produced not only while the A6 gene is being expressed. Such antisense DNA may be expressed constitutively, under the control of any appropriate promoter.

According to a further aspect of the invention, therefore, there is provided antisense nucleic acid which includes a transcribable strand of DNA complementary to at least part of the strand of DNA that is naturally transcribed in a gene encoding a callase enzyme, such as a 53 kDa callase enzyme in *B. napus* or an equivalent protein in another member of the family Brassicaceae.

Antisense DNA in accordance with this aspect of the invention may be under the control of any suitable promoter which permits transcription during, but not necessarily only during, tapetum development. As indicated above, the promoter may therefore be constitutive, but the use of a tapetum-specific promoter such as A3 or A9 as described above in relation to the second aspect of the invention is certainly not excluded and may be preferred for even greater control. Such antisense DNA would generally be useful in conferring male sterility on members of the family Brassicaceae.

A still further example of male sterility DNA encodes an RNA enzyme (known as a ribozyme) capable of highly specific cleavage against a given target sequence (Haseloff and Gerlach *Nature* 334 585–591 (1988). Like antisense DNA, ribozyme DNA (coding in this instance for a ribozyme which is targeted against the RNA encoded by the A6 gene) does not have to be expressed only at the time of expression of the A6 gene. Again, it may be possible to use any appropriate promoter to drive ribozyme-encoding DNA, including one which is adapted for constitutive expression.

According to a further aspect of the invention, there is therefore provided DNA encoding a ribozyme capable of specific cleavage of RNA encoded by a gene encoding a callase enzyme, such as a 53 kDa callase enzyme in *B. napus* or an equivalent protein in another member of the family Brassicaceae. Such ribozyme-encoding DNA would generally be useful in conferring male sterility on members of the family Brassicaceae.

In preferred embodiments of DNA sequences of this invention, including those comprising the A6 promoter-male sterility DNA construct, 3' transcription regulation signals, including a polyadenylation signal, may be provided. Preferred 3' transcription regulation signals are derived from the Cauliflower Mosaic Virus 35S gene. It should be recognised that other 3' transcription regulation signals could also be used.

The antisense nucleic acid and ribozyme-encoding nucleic acid described above are examples of a more general principle: according to another aspect of the invention, there is provided DNA which causes (for example on its expression) selective disruption of the proper expression of the callase, or in preferred embodiments A6, gene.

Recombinant DNA in accordance with the invention may be in the form of a vector. The vector may for example be a plasmid, cosmid or phage. Vectors will frequently include one or more selectable markers to enable selection of cells transfected (or transformed: the terms are used interchangeably in this specification) with them and, preferably, to enable selection of cells harbouring vectors incorporating heterologous DNA. Appropriate start and stop signals will generally be present. Additionally, if the vector is intended for expression, sufficient regulatory sequences to drive expression will be present; however, DNA in accordance with the invention will generally be expressed in plant cells, and so microbial host expression would not be among the primary objectives of the invention, although it is not ruled out. Vectors not including regulatory sequences are useful as cloning vectors.

Cloning vectors can be introduced into *E. coli* or another suitable host which facilitate their manipulation. According to another aspect of the invention, there is therefore provided a host cell transfected or transformed with DNA as described above.

DNA in accordance with the invention can be prepared by any convenient method involving coupling together successive nucleotides, and/or ligating oligo- and/or polynucleotides, including in vitro processes, but recombinant DNA technology forms the method of choice.

Ultimately, DNA in accordance with the invention (whether (i) A6 promoter plus male sterility gene, (ii) antisense DNA to A6 gene or ribozyme DNA targeted to A6 RNA) will be introduced into plant cells, by any suitable means. According to a further aspect of the invention, there is provided a plant cell including DNA in accordance with the invention as described above.

Preferably, DNA is transformed into plant cells using a disarmed Ti-plasmid vector and carried by Agrobacterium by procedures known in the art, for example as described in EP-A-0116718 and EP-A-0270822. Alternatively, the foreign DNA could be introduced directly into plant cells using an electrical discharge apparatus. This method is preferred where Agrobacterium is ineffective, for example where the recipient plant is monocotyledenous. Any other method that provides for the stable incorporation of the DNA within the nuclear DNA of any plant cell of any species would also be suitable. This includes species of plant which are not currently capable of genetic transformation.

Preferably DNA in accordance with the invention also contains a second chimeric gene (a "marker" gene) that enables a transformed plant containing the foreign DNA to be easily distinguished from other plants that do not contain the foreign DNA. Examples of such a marker gene include antibiotic resistance (Herrera-Estrella et al, *EMBO J.* 2, 987–995 (1983)), herbicide resistance (EP-A-0242246) and glucuronidase (GUS) expression (EP-A-0344029). Expression of the marker gene is preferably controlled by a second promoter which allows expression in cells other than the tapetum, thus allowing selection of cells or tissue containing the marker at any stage of regeneration of the plant. The preferred second promoter is derived from the gene which encodes the 35S subunit of Cauliflower Mosaic Virus (CaMV) coat protein. However any other suitable second promoter could be used.

A whole plant can be regenerated from a single transformed plant cell, and the invention therefore provides transgenic plants (or parts of them, such as propagating material) including DNA in accordance with the invention as described above. The regeneration can proceed by known methods. When the transformed plant flowers it can be seen to be male sterile by the inability to produce viable pollen. Where pollen is produced it can be confirmed to be non-viable by the inability to effect seed set on a recipient plant.

Male fertility curtailed by means of the present invention may be restored by an appropriate restoration system, whose nature will correspond to the particular manner used to render the plant male-sterile. Specific and preferred restoration systems described below are based on different mechanisms: antisense RNA and ribozymes.

antisense RNA: where the disrupter gene encodes a non-anther mRNA, such as the mRNA for the protein actinidin, restoration is provided by crossing into the male-sterile plant a gene encoding an anti-sense RNA specific to the disrupter mRNA driven by a tapetum-specific promoter with the appropriate temporal regulation. This will lead to the destruction of the sense mRNA and restore fertility. This approach is not applicable where the disrupter is prematurely expressed callase since expression of a callase anti-sense RNA will lead to the destruction of both the target disrupter callase mRNA and the normal callase mRNA which is required for microspore release and the production of viable pollen grains. Thus fertility would not be restored.

ribozymes: this approach is more generally applicable since the target site for ribozymes is small and therefore can be engineered into any mRNA. This allows in principal any introduced mRNA to be specifically targeted for destruction. Thus mRNAs encoding non-specific disrupter functions such as actinidin are destroyed and fertility restored by crossing in a gene encoding ribozymes specific to the actinidin mRNA. Where the disrupter is callase, restoration is achieved by crossing in genes encoding ribozymes specific to a short synthetic sequence introduced into the non-translated leader of the prematurely expressed disrupter callase mRNA. Since this sequence is not present in the normal unmodified callase mRNA correctly timed callase activity is unaffected and fertility is restored.

Some preferred features of the invention have been described only in relation to one aspect of it. It will be appreciated that preferences extend to all aspects of the invention mutatis mutandis.

BRIEF DESCRIPTION OF THE DRAWINGS

FIG. 1 shows the DNA sequence of the *B. napus* cDNA A6 (SEQ ID NO: 11) together with the deduced protein sequence of the ORF contained in A6 (SEQ ID NO: 12);

FIG. 2 shows an alignment of the deduced primary structure of the *B. napus* and *A. thaliana* A6 genes with the primary structure of previously described glucanases; the following is a key:

Bn A6 (SEQ ID NO: 18): 53 kDa anther-specific protein of *B. napus*

At G62(SEQ ID NO: 17): Corresponding A6 protein from *A. thaliana*

NPGLUC (SEQ ID NO: 13): Tobacco β-1,3 glucanase (basic) (De Loose et al., *Gene* 70 13–23, (1988)

BEAN (SEQ ID NO: 14): Bean β-1,3 glucanase Edington et al., *Plant Mol. Biol.* 16, 81–94 (1991)

PR-Q (SEQ ID NO: 15): Tobacco β-1,3 glucanase (extracellular) (Payne et al., *Plant Mol. Biol.* 15 797–808 (1990)

Figure 3:
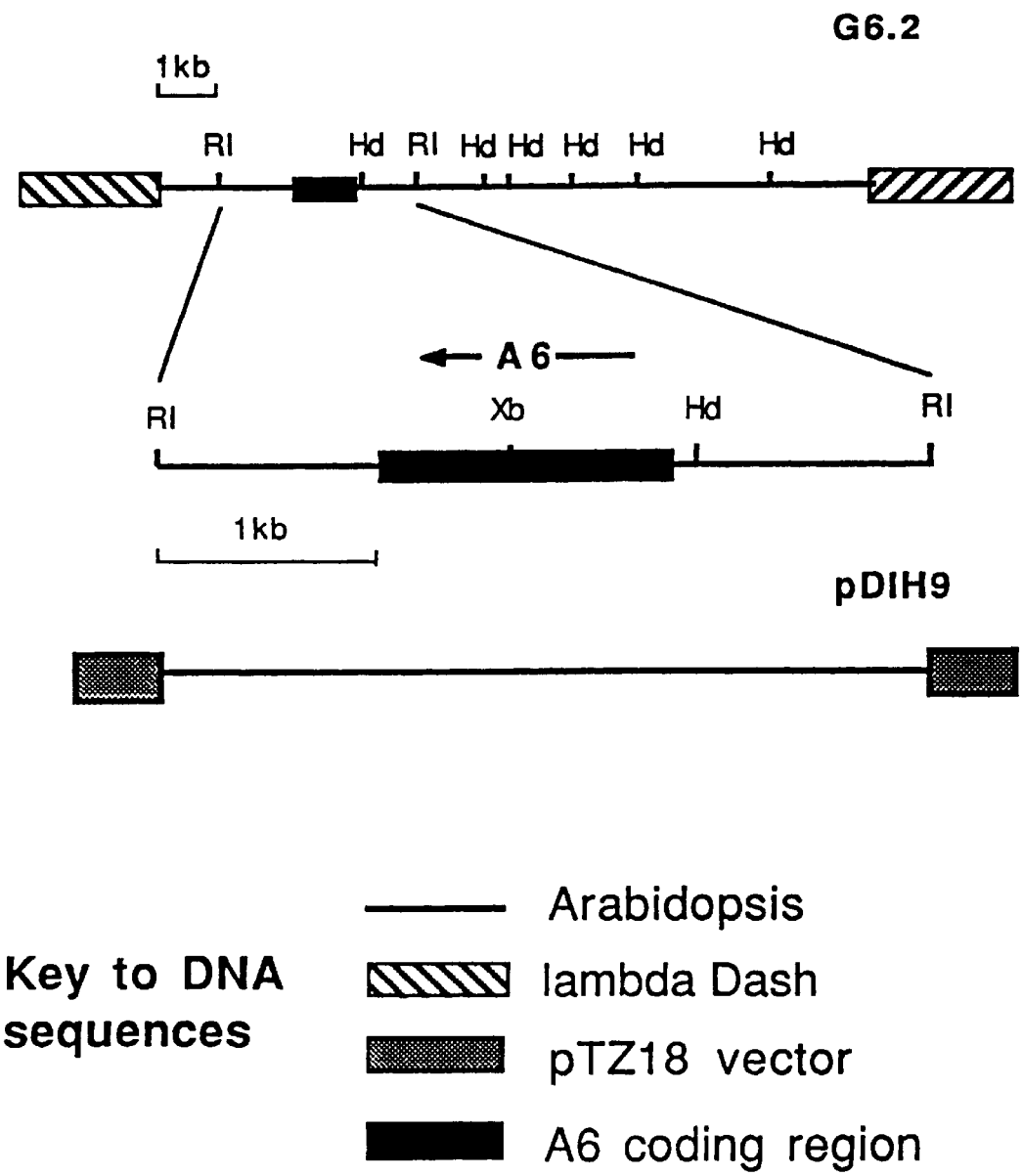
Figure 6:
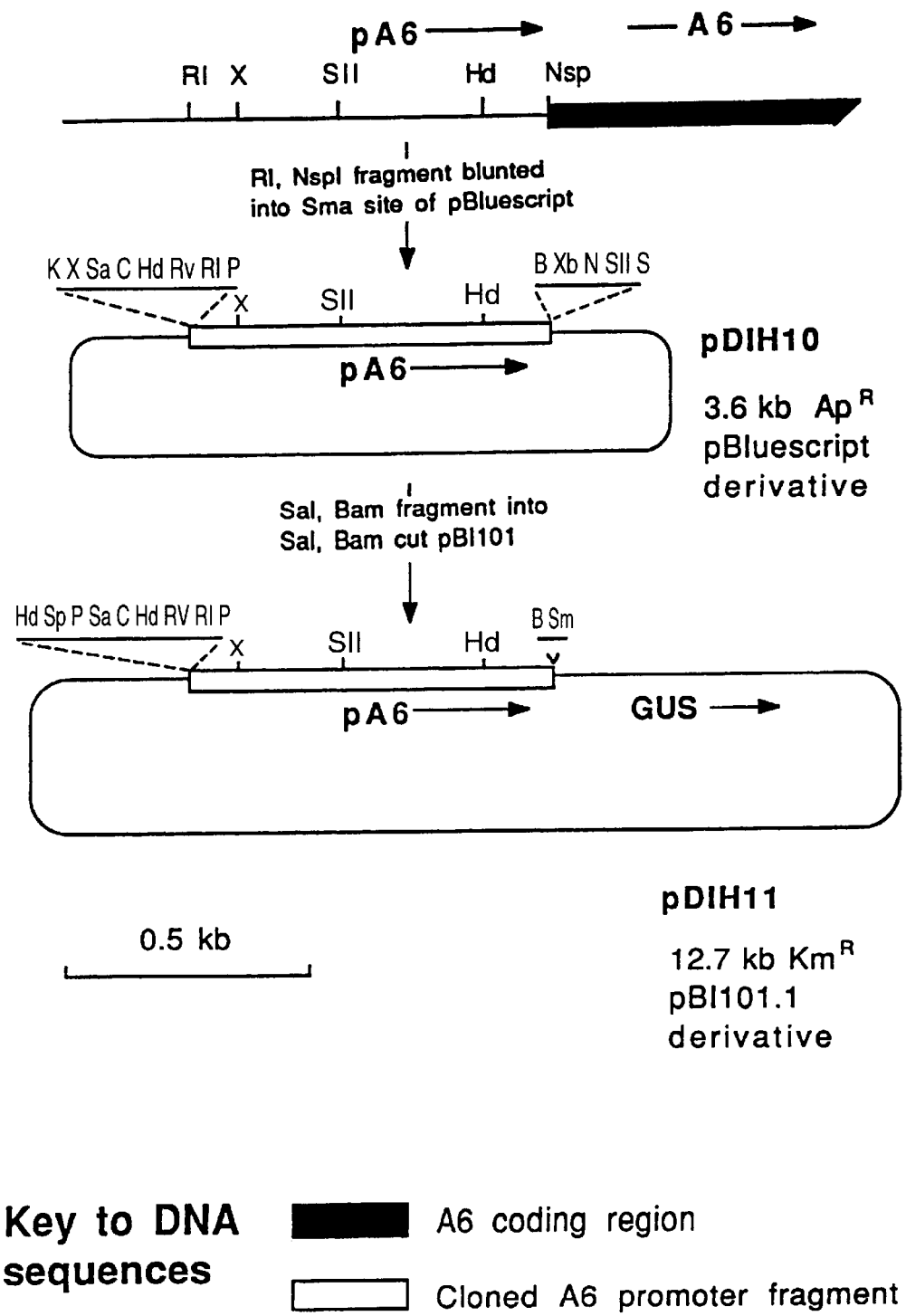
Figure 7A:
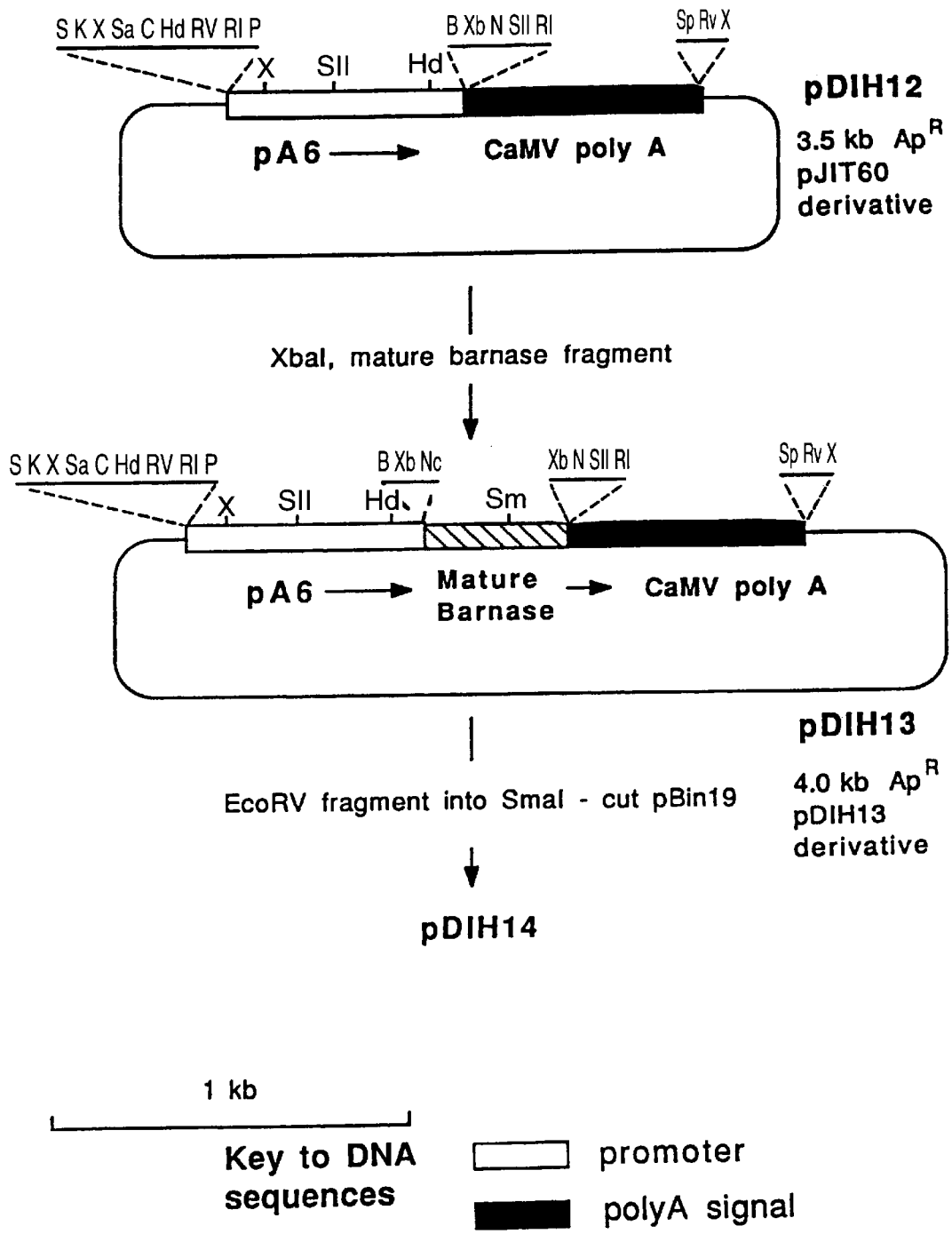
Figure 7B:
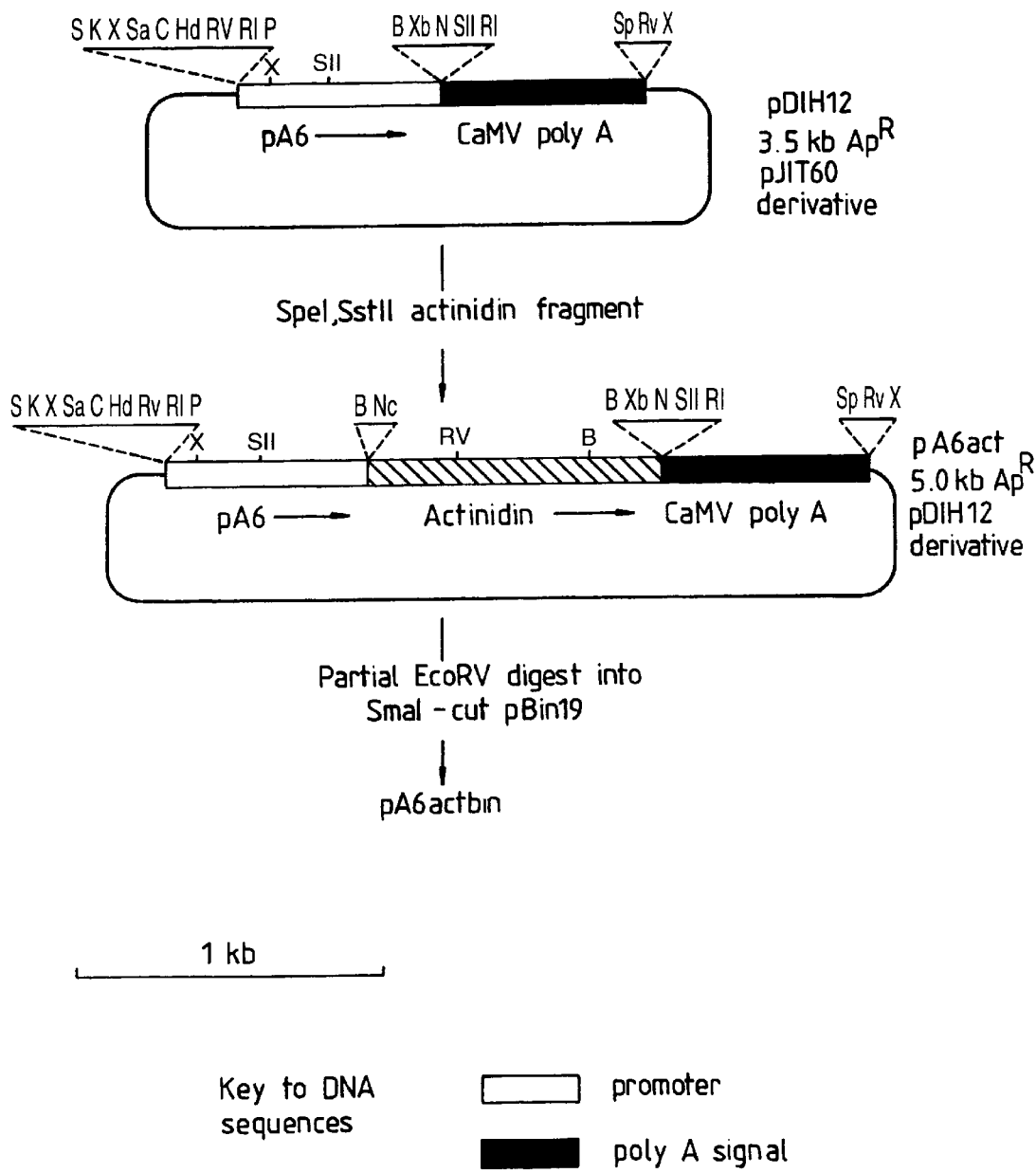
Figure 8B:
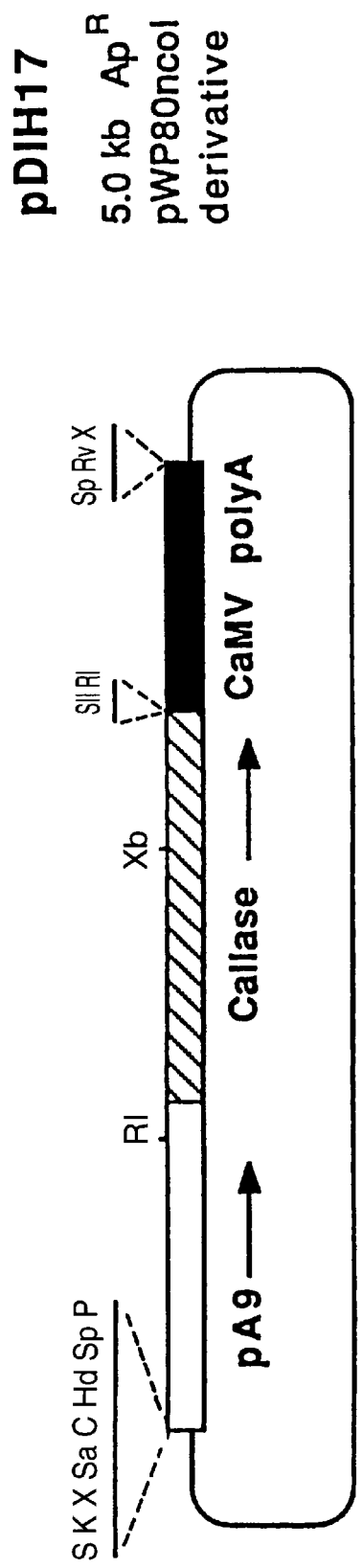
Figure 8C:
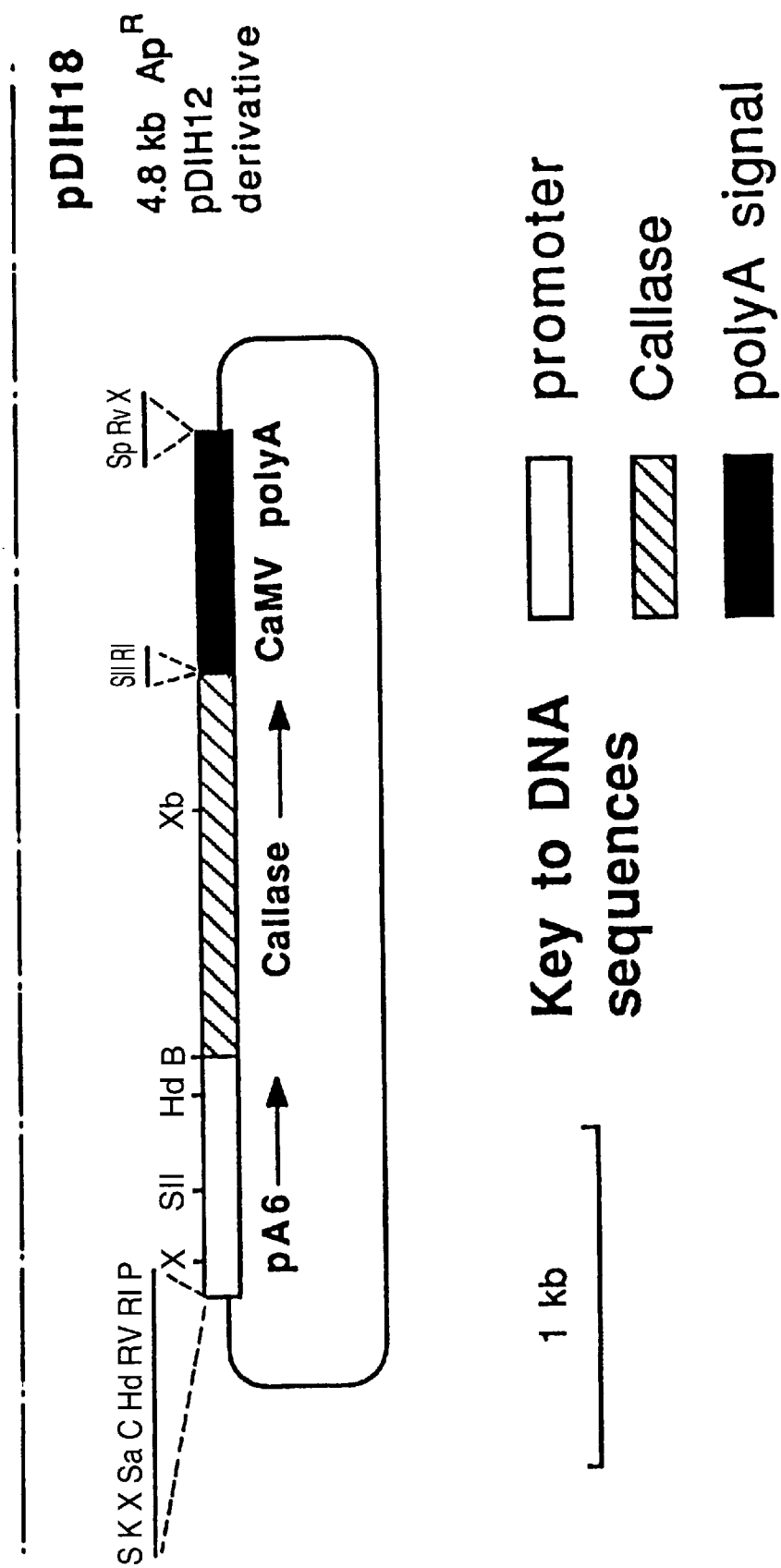
Figure 9:
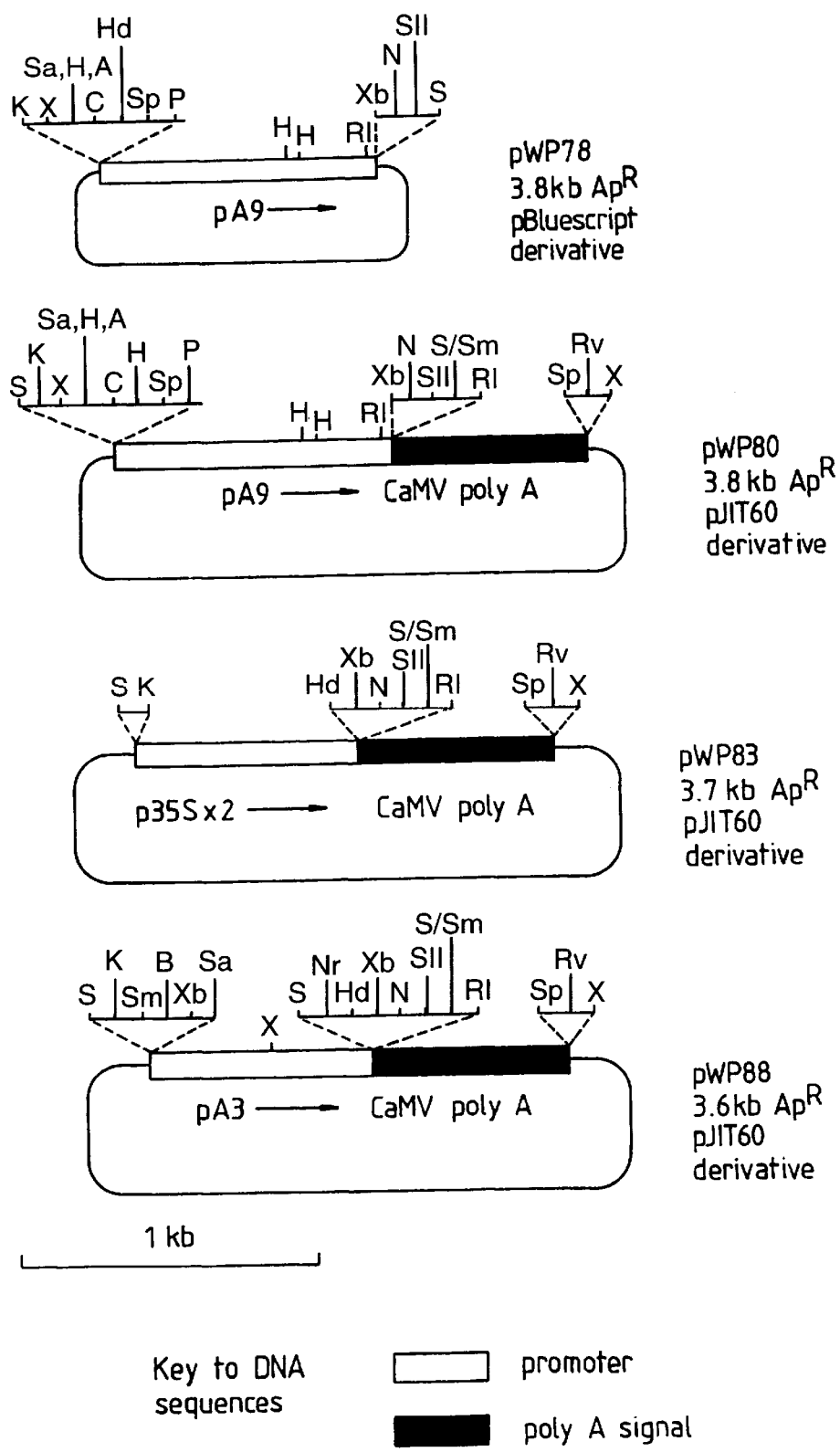

BARLEY (SEQ ID NO: 16): Hoj et al., *Plant Mol. Biol.* 13, 31–42 (1989);

FIG. 3 shows a restriction enzyme map of the *A. thaliana* genomic clone G6.2. Only relevant sites are shown and these may not be unique in G6.2. The position of the coding region of A6 is indicated as a filled box. Also the extent of the insert cloned into the plasmid pDIH9 is shown;

FIG. 4 shows the DNA sequence (SEQ ID NO: 19) and putative primary structure of the *A. thaliana* A6 gene (SEQ ID NO: 20). The underlined sequence conforms to a TATA box motif;

FIG. 5*a* shows a comparison of the DNA sequences of the *B. napus* cDNA A6 (SEQ ID NO: 22) with the *A. thaliana* A6gene (SEQ ID NO: 21). The underlined trinucleotides indicate the start and stop positions of the A6 coding sequences;

FIG. 5*b* shows a comparison of the putative polypeptide encoded by *B. napus* cDNAs A6 (SEQ ID NO: 24) with that encoded by the *A. thaliana* A6 (SEQ ID NO: 23) gene;

FIG. 6 shows the construction of a chimeric gene containing a transcriptional fusion between the A6 promoter and an *E. coli* gene encoding β-glucuronidase;

FIG. 7*a* refers to Example 3*a* and shows the construction of a chimeric gene containing a transcriptional fusion between the A6 promoter and a sequence encoding mature barnase;

FIG. 7*b* refers to Example 3*b* and shows the construction of a chimeric gene containing a transcriptional fusion between the A6 promoter and a sequence encoding actinidin;

FIG. 8 shows the construction of chimeric genes between tapetum-specific promoters and *A. thaliana* callase: a) Transcriptional fusion between the A9 promoter and callase; b) Transcriptional fusions between the A9 and A6 promoters with callase lacking the sequence encoding the protein's C-terminal extension; and FIG. 9 shows the construction of plasmids pWP80, pWP83 and pWP88.

Abbreviations used for restriction enzymes in the drawings are:

B, BamHI; Bg, BglII; C, ClaI; Hd, HindIII; K, KpnI; N, NotI; Nc, NcoI; Np, NspI; Nr, NruI; P, PstI; RI, EcoRI; RV, EcoRV; S, SstI; Sa, SalI; Sp, SphI; Sm, SmaI; SII, SacII; X, XhoI; Xb, XbaI.

DETAILED DESCRIPTION OF THE INVENTION

EXAMPLE 1

Isolation of a cDNA encoding the anther-specific β(1,3) glucanase (callase) from *Brassica napus* and isolation of the corresponding gene from *Arabidopsis thaliana*

Anther-specific cDNAs have been isolated by differential screening of *Brassica napus* cDNA libraries constructed from RNA extracted from dissected anthers as described below (Scott et al, *Plant Mol. Biol.* in press). cDNA clone A6 was isolated from a library constructed from anthers that were 1.8–2.0 mm in length. This library was constructed in the vector Lambda ZapII (Stratagene). The A6 cDNA was used as a probe to isolate homologous genes from an *A. thaliana* genomic library constructed in the vector Lambda Dash (Stratagene).

Materials and methods

Plant material. All seeding material for nucleic acid isolation was obtained from 2–3 week old plants grown in a controlled environment growth cabinet with 18 h photoperiod at 24° C. Seedling RNA for differential screening and Northern blot analysis was obtained from *B. napus* oleifera var. "Topaz". Male fertile buds were collected from field grown plants of *B. napus* oleifera var. "Lictor" (Nickersons Seeds, Cambridge, UK). Male-sterile buds were obtained from field grown B. napus var. CMS "ogura" (Nickersons Seeds, Cambridge, UK) plants.

Dissection of anthers. For cDNA library construction, flower spikes were quickly harvested and kept at 4° C. until required, but no longer than 5 h. Anthers were dissected from appropriately sized buds using fine forceps and immediately frozen in liquid nitrogen.

Collection of buds. Large samples of complete whorls of buds, at a stage immediately prior to the opening of first flowers, were frozen in liquid nitrogen and stored at −80° C.

Cytological staging of anthers and buds. The developmental stage of buds of predetermined length was assessed by light microscopic examination of sporogenous cells, microspores or pollen grains extruded from whole anthers squashed in the presence of aceto-orcein or acridine orange. Accurate determination of bud length was performed using a low-powered light microscope equipped with a calibrated eyepiece graticule. Bud lengths stated were measured from the base of the pedicle to the tip of the outermost sepal.

RNA isolation and analysis. Material intended for low resolution Northern dot blot analysis or for mRNA isolation was ground to a fine powder in a mortar cooled with liquid nitrogen. Total RNA was isolated from the powder using a phenol based method as described previously (Draper et al "Plant Genetic Transformation and Gene Expression: A Laboratory Manual", Blackwell Scientific Publishers, Oxford (1988)). Poly(A)$^+$ RNA was purified by two rounds of oligo(dT)-cellulose chromatography essentially as described in the Maniatis et al manual. RNA for high resolution dot blots was isolated according to the method of Verwoerd et al, *Nuc. Acids Res.* 17 2362 (1989)).

cDNA library construction and screening. cDNAs were synthesised from poly(A)$^+$ RNA using (Amersham) or (Pharmacia) cDNA synthesis kits, according to the manufacturers instructions. cDNAs were ligated into EcoRI cleaved dephosphorylated lambda Zap I (Stratagene) ("sporogenesis" library) or lambda Zap II (Stratagene) ("microspore-development" library) and packaged using Amersham in vitro packaging extracts. (When cloning into lambda Zap II, EcoRI linkers (Pharmacia Ltd) were used; these linkers also contain internal NotI sites, so the entire cDNA can be recovered as a NotI fragment, providing that the cDNA contains no internal NotI sites.) Clones were screened differentially, on duplicate HYBOND-N filters (Amersham) with [$^{32}$P]-labelled single-stranded cDNA probe prepared from either the appropriate anther poly(a)$^+$ RNA or seedling poly(A)$^+$ RNA according to Sargent *Methods in Enzymol.* 152 423–432 (1987)). (The expression HYBOND-N is a trade mark.)

RNA dot and gel blots. Total RNA for dot-blots was spotted onto HYBOND N (Amersham) according to the manufacturers instructions. Northern gels were run and RNA transferred to HYBOND-N according to Fourney (*BRL Focus* 10 5–7 (1988)). Hybridisation and washing of HYBOND-N filters was according to manufacturers instructions.

In situ hybridisation. For embedding and sectioning *B. napus* buds were frozen in CRYO-M-BED (TAAB Laboratories Equipment Ltd). (The expression CRYO-M-BED is a trade mark.) Sections were cut nominally 10 µm thick, mounted on subbed slides (Van Prooijen-Knegt et al *Histochemical J.* 14 333–344 (1983)) fixed in 4% paraformaldehyde and dehydrated. [$^{35}$S]rUTP (>1000 Ci/mmol, Amersham SJ.1303) labelled sense and anti-sense RNA probes were transcribed from the T3 and T7 promoters of BLUESCRIPT SK$^-$ (Stratagene), in which the cDNAs are cloned.

(The expression BLUESCRIPT SK$^-$ is a trade mark.) Following transcription, probes were cleaved by alkaline hydrolysis to generate probe fragments approximately 150 bp in length. The hybridisation solution was 50% formamide, 300 mM NaCl, 10 mM Na$_2$HPO$_4$ pH 6.8, 10 mM Tris-HCl pH 7.5, 5 mM EDTA, 0.02% bovine serum albumin, 0.02% Ficoll, 0.02% polyvinylpyrrolidone, 10 mM dithiothreitol, 10% dextran sulphate, 0.7 mg/ml *E. coli* tRNA, 50–100 ng/ml probe stock (6.7×10$^5$ cpm/ng probe). Sections were hybridised in 30 µl hybridisation solution at 50° C. for 16 h. Slides were washed 3×1 h at 50° C. in 50% formamide, 300 mM NaCl, 10 mM Na$_2$HPO$_4$ pH 6.8, 10 mM Tris-HCl pH 7.5 and then rinsed in RNase A buffer to remove formamide. RNase A treatment, (150 µg/ml RNase A in 500 mM NaCl, 10 mM Tris HCl pH 7.5), was carried out at 37° C. for 1 h. The slides were then washed twice in 2×SSC (0.3M NaCl, 0.03M Na citrate, pH 7.0) at 65° C. for 30 min, dehydrated through graded alcohols and dried. For autoradiography, slides were dipped at 45° C. in ILFORD K5 nuclear track emulsion (1 g/ml in 1:59 glycerol:water mix). (The expression ILFORD K5 is a trade mark.) Exposure time was between 2 and 14 days. Development was in KODAK D19. (The expression KODAK D19 is a trade mark.) Following development sections were stained with methylene blue and made permanent.

a) Analysis of the *B. napus* A6 cDNA.

Northern hybridisation analysis using RNA extracted from *B. napus* anthers, pollen, carpels and seedlings indicated that A6 was only expressed in anthers of length 1.5–2.0 mm with maximal expression at about 1.8 mm. Thus A6 temporal expression spans the period in anther development when the microsporocytes are in meiotic division to early microspore interphase. The A6 cDNA is 1532 bp in length and contains an open-reading frame (ORF) extending from position 1–1424 bp (FIG. 1) suggesting that this clone is not full-length. The estimated size of *B. napus* A6 mRNA from Northern gel blots is about 1700 bp, again suggesting that this clone is not full-length. The ORF encodes a polypeptide of 474 amino-acids with a molecular weight of 53 kda, which is homologous to pathogenesis-related (PR) and other previously characterised β(1,3)-glucanases (FIG. 2) strongly suggesting that A6 encodes the anther-specific β(1,3) glucanase (callase). As will be described in Example 6 below, the production of antisense RNA to the A6 transcript in anthers of transgenic plants produces male sterile plants. These plants have a phenotype that is consistent, at the biochemical and cytological level, with the assertion that A6 encodes callase.

The alignment of A6 with β(1,3) glucanases shows that A6 is significantly larger due to the presence of a long C-terminal extension, the beginning of this extension corresponding to the C-terminus of mature β(1,3) glucanase enzymes. The level of homology of A6 to other glucanases although very significant (33% identity over the region of homology) is however lower than that seen between the most divergent previously isolated β(1,3) glucanases (51% identity). Thus the A6 protein is not recognised by antibodies raised to the acidic PR glucanase of tomato or to the basic hormonally induced β(1,3) glucanase of tobacco. No hybridisation is observed to *B. napus* anther RNA or to the *B. napus* cDNA library using $^{32}$P labelled *A. thaliana* genomic glucanase sequences (provided by F. Ausubel) or using $^{32}$P labelled pGL43, a clone containing a basic β(1,3) glucanase from *N. tabacum* (Shinshi et al. *Proc. Natl. Acad. Sci. USA* 85, 5541–5545 (1988)). Thus it is not possible to clone anther-specific callases by using available β(1,3) glucanase sequences or antibodies. However the alignment of A6 with other glucanases shown in FIG. 2 enables the identification of amino-acids that are likely to be conserved in all glucanases. This allows the design of oligonucleotides that will be specific probes for β(1,3) glucanases and thus enable the cloning of the anther-specific glucanase cDNAs or genes from other plant species. Callase can be distinguished from other β(1,3) glucanases by virtue of its unique spatial and temporal pattern of expression coupled with the possession of a longer C-terminal extension than other β(1,3) glucanases.

b) Isolation and characterisation of homologous genes to A6 in *A. thaliana*.

Two genomic clones were isolated from an *A. thaliana* genomic library that hybridised to the *B. napus* A6 cDNA. One, G6.2, was analysed in detail (FIG. 3). A 3.2 kb EcoRI fragment was subcloned into EcoRI-cut pTZ18U (Pharmacia) forming pDIH9 (FIG. 3), and the coding region of A6 and 881 bp upstream was sequenced (FIG. 4). Comparison of the *B. napus* and *A. thaliana* A6 sequences showed that they were 85% identical in the coding regions (FIG. 5a) at the nucleotide level and 83% identical at the protein level (FIG. 5b). The sequence alignment shows that the ORF encoded by the *B. napus* cDNA is almost full-length and probably lacks about 5 residues at the N-terminus. The *A. thaliana* A6 gene encodes a product of 479 amino-acids with a predicted molecular weight of 53.7 kDa. The A6 proteins have a hydrophobic N-terminal sequence that conforms to the rules defined by von Heijne, (*J. Mol. Biol.* 184, 99–105 (1985)) for signal sequences. Callase is secreted from the tapetum into the anther locule and therefore should possess such a sequence.

The other genomic clone isolated (G6.1) was partially sequenced and was shown to be virtually identical to G6.2 both within the A6 coding region and also within the putative A6 promoter region.

EXAMPLE 2

The use of the A6 promoter to drive the expression of Glucuronidase in anthers of *Arabidopsis thaliana, Brassica napus, Hordeum vulgare, Nicotiana tabacum* and *Zea mays*

To demonstrate that the putative promoter region of A6 is capable of driving the expression of a foreign gene in *A. thaliana, B. napus, H. vulgare* and *N. tabacum* a transcriptional fusion of the promoter was made to the *Escherichia coli* gene encoding β-glucuronidase (GUS). An 844 bp EcoRI-NspI fragment (position 1–884 bp in FIG. 4) containing the putative A6 promoter is excised from pDIH9 and the ends rendered blunt with Klenow. This fragment is cloned into the SmaI site of pBluescript forming pDIH10 (FIG. 6). The A6 promoter is then cloned as a SalI, BamHI fragment into pBI101.1 (Jefferson et al., *EMBO. J.* 6, 3901–3907 (1987)) forming pDIH11 (FIG. 6). This plasmid contains the A6 promoter transcriptionally fused to GUS. pDIH11 is then transformed into *N. tabacum, A. thaliana, B. napus, H. vulgare* and *Z. mays* using standard transformation techniques. Transformation of *H. vulgare* is achieved using a microprojectile gun. Analysis of transformed plants demonstrates that GUS activity is localised to anther tissues, specifically to tapetal cells. The temporal regulation of GUS activity is identical to the temporal expression observed for the A6 genes as described in Example 1. The A6 promoter drives transcription in tapetal cells through a period commencing at the meiocyte stage of development and terminating during early microspore interphase.

The use of the A6 promoter to create male sterile plants.

Tapetum-specific promoters can be employed in a variety of ways to generate male sterile plants. For example, male sterility can be achieved by using the tapetum-specific promoter to express antisense and sense transcripts corresponding to tapetal messages (see Example 6), drive the premature expression of glucanase activity (see Example 4) and drive the expression of cytotoxic agents such as proteases and nucleases.

EXAMPLE 3

Construction of a chimeric A6-Barnase gene and a chimeric A6-actinidin gene and their expression in transgenic plants To demonstrate the utility of the A6 promoter it is used to drive the expression of the RNAase, barnase, and the protease, actinidin, in tapetal cells.

EXAMPLE 3A

Construction and expression in transgenic plants of chimeric gene fusion between the tapetum-specific A6 promoter and barnase To demonstrate the utility of the A6 promoter it is used to drive the expression of the RNAase, barnase, in tapetal cells. Use of the barnase gene to create male sterile plants has been described in patent application EP-A-0344029 (Plant Genetic Systems) and has been published by Mariani et al. *Nature* 347, 737–741.

The oligonucleotide primers

5' GGGTCTAGACCATGGGCACAGGTTAT-CAACACGTTTGACGGG 3' (SEQ ID NO: 1) and

5' GTAAAACGACGGCCAGTGCC 3' (SEQ ID NO: 2) are used in a polymerase chain reaction (PCR) to generate a fragment encoding barstar and the mature barnase product from the plasmid pTG2 (Horovitz et al. *J. Mol. Biol.* 216, 1031–1044 (1990)). The first primer is homologous to nucleotides 195–221 bp of FIG. 1 in Hartley R.W. *J. Mol. Biol.* 202, 913–915. The second primer is homologous to a sequence immediately next to the HindIII site of pTZ18U (Pharmacia). The PCR fragment is digested with XbaI and cloned into XbaI-cut pDIH12 forming pDIH13 in which the A6 promoter is transcriptionally fused to the mature barnase sequence (FIG. 7). (pDIH12 is constructed by cloning the KpnI, XbaI fragment of pDIH10 (FIG. 6) into KpnI, XbaI-cut pWP80 (see below and WO-A-9211379).) This gene fusion is transferred to pBin19 (*Bevan* et al 1984) by ligating the EcoRV fragment of pDIH13 to SmaI-cut pBin19. The pBin19 derivative plasmid is transformed into *N. tabacum, B. napus, H. vulgare* and *Z. mays* where expression of barnase in transgenic plants results in the degradation of the tapetal and microsporocyte cells of the anther causing male sterility.

Plasmids pWP80, pWP83 and pWP88 pWP80, an intermediate vector designed to express sense and anti-sense RNA using the *A. thaliana* tapetum-specific A9 promoter, was constructed as follows. The isolation of the *A. thaliana* tapetum-specific A9 promoter is described in WO-A-9211379. To construct pWP80, pWP72 (WO-A-9211379) is digested with XbaI and religated, thus removing the BamHI site in the polylinker and forming pWP78 (FIG. 9). The KpnI, SstI (the SstI end rendered blunt with Klenow) A9 promoter fragment of pWP78 is ligated into KpnI, SmaI-cut pJIT60, forming pWP80 (FIG. 9). This intermediate vector consists of a 936 bp A9 promoter fragment fused to a polylinker derived from pBluescript with a 35S CaMV polyadenylation signal. pJIT60 is identical to pJIT30 (Guerineau et al., *Plant Mol. Biol.* 15, 127–136 (1990)) except that the CaMV 35S promoter of pJIT30 is replaced by a double 35S CaMV promoter.

pWP83, an intermediate vector to express sense and antisense RNA using the constitutive CaMV 35S promoter, was constructed as follows. The A9 promoter of pWP80 is replaced by a 'double' CaMV 35S promoter by cloning the 785 bp KpnI, XbaI fragment of pJIT60 into KpnI, XbaI-cut pWP80, forming pWP83 (FIG. 9).

pWP88, an intermediate vector to express sense and antisense RNA using the A3 promoter, was constructed as follows. The isolation of the A. thaliana tapetum-specific A3 promoter is described in WO-A-9211379. The CaMV promoter of pWP83 is replaced with the A3 promoter by cloning the 745 bp KpnI, HindIII fragment of pWP87 (WO-A-9211379) into KpnI, HindIII-cut pWP83, forming pWP88 (FIG. 9).

pWP80, pWP83 and pWP88 are therefore identical apart from the promoter region and surrounding restriction enzyme sites.

EXAMPLE 3B

Construction and expression in transgenic plants of chimeric gene fusion between the tapetum-specific A6 promoter and actinidin The entire cDNA clone encoding actinidin is isolated as an EcoRI, BamHI fragment from pKIW1450 (Podivinsky et al, *Nuc. Acids Res.* 17, 8363 (1989)) and is recloned into EcoRI, BamHI-cut pBluescript KS- (Stratagene) forming pWP100. The oligonucleotide primers 5' GGGACTAGTCCATGGGTTTGCCCAAATCC 3' (SEQ ID NO: 3) and

5' AATACGACTCACTATAG 3' (SEQ ID NO: 4)

are used in a PCR reaction to generate a DNA fragment containing the entire coding region of actinidin, but with the sequence immediately before the initiating 'ATG' of the gene mutated to an SpeI site. The first primer is complementary to positions 38–55 bp of FIG. 1 (Podivinsky et al 1989), and the second is homologous to a sequence immediately next to the KpnI site of pBluescript KS-. This PCR fragment is digested with SpeI and SstII and cloned into XbaI, SstII-cut pDIH12 forming pA6act (FIG. 7B). The A6-actinidin chimeric gene is then recovered as a EcoRV fragment obtained by a partial EcoRV digest of pA6act and cloned into SmaI-cut pBin19 (Bevan et al 1984). The pBin19 derivative plasmid is transformed into *N. tabacum, B. napus* and *H. vulgare* where expression of actinidin in transgenic plants results in male sterility.

EXAMPLE 4 to 9

Use of the coding sequence of the A6 gene to produce male sterile plants

EXAMPLE 4A

Construction and expression in transgenic plants of chimeric gene fusion between the tapetum-specific promoter A9 and the A6 gene The temporal pattern of expression of the tapetum-specific A3 and A9 genes determined from Northern analysis and promoter-GUS fusions show that both promoters are active at stages of anther development prior to the release of microspores from tetrads (see WO-A-9211379). Thus either promoter is suitable for driving the premature expression of β(1,3) glucanase in anthers leading to male sterility (see discussion earlier in description). Chimeric fusions between these promoters and either the *B. napus* A6 cDNA or the *A. thaliana* A6 gene coding region can be constructed. In FIG. 8a the construction of an A9 promoter fusion to the *A. thaliana* A6 gene is shown. Oligonucleotide primers are designed to the 5' untranslated leader sequence of the *A. thaliana* gene and to the 3' end of this gene such that a complete A6 gene can be obtained by use of the polymerase chain reaction from pDIH9. The primers are engineered with the restriction sites SpeI and SstII for cloning the PCR A6 gene into vectors containing the tapetum-specific promoters. The 5' primer also contains a GTC sequence (underlined) which, in RNA, is a target for clevage by a ribozyme described in Example 5.

The 5' oligonucleotide sequence is:

5' GGGACTAGTGTCACGCTGACAAAGACAT-GTCTCTTC 3' (SEQ ID NO: 5)

The 3' sequence is:

5' CCCCGCGGTCACAGAGTAACGCTCG-GAAACTTGC 3' (SEQ ID NO: 6)

The A6 PCR fragment is cloned as an 1548 bp SpeI, SstII fragment into XbaI, SstII-cut pWP80 (see WO-A-9211379), forming a transcriptional fusion between the A9 and A6 genes (FIG. 8a). This construct is transferred to pBin19 as a SstI, XhoI fragment.

EXAMPLE 4B

Construction and expression in transgenic plants of chimeric gene fusions of the A9 or the A6 promoter to the A6 gene which lacks the sequences encoding the C-terminal extension of the anther-specific glucanase The A6 protein has a long C-terminal extension when aligned against other previously sequenced plant glucanases (FIG. 2). Extracellular glucanases do not have C-terminal extensions in contrast to those known to be located in the plant vacuole. The C-terminal extension in the anther-specific glucanase may thus be required for targeting to an intracellular storage body prior to its release into the locule. Removal of the C-terminal extension of A6 may lead to the immediate export of the glucanase into the locule, so that the A6 promoter in addition to the A3 and A9 promoters will cause male sterility when expressing such a construct. FIG. 8b shows the construction of a chimeric genes between the A9 and A6 promoters and the anther-specific glucanase that lacks the C-terminal extension. The oligonucleotide primers:

5' GGGACTAGTGTCACGCTGACAAAGACAT-GTCTCTTC 3' (SEQ ID NO: 7) and

5' CCCCGCGGTTAGAAATCTACGTGTAGATTGG 3' (SEQ ID NO: 8)

are used to PCR an 1208 bp fragment from pDIH9. This is either cloned as an SpeI, SstII fragment into pWP80 or as an SpeI, SstII fragment into pDIH12. Both chimeric genes are transferred to pBin19.

All the pBin19 constructs are transformed into *N. tabacum, B. napus* and *H. vulgare*. The transgenic plants are male-sterile.

EXAMPLE 5

Restoration of fertility of plants described in Example 4

Restoration of fertility is achieved by crossing the male sterile plants with transgenic plants that express in the tapetum a ribozyme that recognises and cleaves the sequence introduced into the 5' leader of the PCR A6 gene (the natural A6 mRNA lacks this sequence and is not cleaved). Cleavage of the leader (3' of the sequence GUC ie 14 bp 5' of the ATG initiating codon of the A6 gene) removes the cap site of the PCR A6 transcript leading to rapid degradation of the PCR A6 mRNA and consequently a restoration of fertility in the F1 progeny.

EXAMPLE 6

Construction of chimeric genes producing sense and antisense RNA to the anther-specific glucanase in transgenic plants The A3 and A9 promoters are transcriptionally active during the period that the anther-specific glucanase is expressed. Thus these promoters in addition to a constitutive promoter (CaMV promoter) and the A6 promoter can be used to express anti-sense and sense RNA to the anther-specific glucanase. As described above, and in WO-A-9211379, the cDNAs isolated from the anther library have terminal adapters that enable the cDNA to be recovered as a NotI fragment. Thus the *B. napus* cDNA is digested with NotI and cloned in both orientations into the NotI sites of pWP80, pWP83, pWP88 (see WO-A-9211379 for these three plasmids) and pDIH12 (FIG. 7). These chimeric genes are transferred to pBin19 and transformed into *N. tabacum, B. napus, H. vulgare* and *Z. mays*. The transgenic plants are male-sterile. Cytological examinations of male sterile plants expressing anti-sense A6 RNA, showed that the release of microspores from the tetrads, which requires the degradation of callose, is delayed compared to wild-type plants or is completely absent. Biochemically, these male sterile plants have reduced or undetectable callase levels in the locule fluid of the anther. Both observations confirm that A6 encodes callase.

EXAMPLE 7
Restoration of fertility of the transgenic plants expressing anti-sense A6 RNA, described in Example 6

Restoration of fertility is achieved in two ways. First the male sterile plants are crossed with plants containing additional copies of the *A. thaliana* A6 gene (the 3.2 kb EcoRI fragment of pDIH9 is transferred to pBin19 and this construct transformed into plants). The additional gene copies overcome the down-regulation of the callase product induced by the expression of antisense A6 RNA, resulting in male fertile F1 progeny. Secondly, restoration of fertility in plants expressing antisense A6 RNA is achieved by crossing these plants with plants homozygous for chimeric gene fusions between a tapetum-specific promoter eg A3, A6 or A9 and a ribozyme directed against a GUC sequence within the antisense A6 RNA transcript at position 787–790 bp (FIG. 1) for example. In the F1 progeny cleavage of the antisense A6 transcript results in destabilisation of the antisense RNA and a consequent restoration of fertility.

EXAMPLE 8
Expression of ribozymes, directed against the callase transcript, in transgenic plants Comparison of the nucleotide sequences of the *B. napus* A6 cDNA and the *A. thaliana* A6 genomic sequence (FIG. 5a) reveals 12 GUC trinucleotides that are shared by both sequences and are potential ribozyme target sequences. Two ribozymes are inserted into the *B. napus* A6 cDNA sequence by site-directed mutagenesis. Single stranded DNA from the plasmid A6, which contains the A6 cDNA cloned into the EcoRI site of BLUESRIPT™ SK⁻ (Stratagene), is annealed to the phosphorylated oligonucleotide primers shown below:

5' CGGCGTCGTAGAGCTTCTGAAGATGGC-CCGGTAGGGCCGAAACATGACCGGC 3' (SEQ ID NO: 9) and

5' CGTTGGCTCCTTCCTGAAGATGGCCCGG-TAGGGCCGAAACCGGTACGCACC 3' (SEQ ID NO: 10)

The first primer encodes a ribozyme that is targeted to cleave the GUC at position 102 bp in FIG. 1 and the second the GUC at position 1169 bp. The underlined portion of the primers encodes the ribozyme.

After annealing, the second DNA strand is completed with nucleotides and Klenow. A plasmid with both ribozyme inserts, detected by duplicate colony hybridizations using the ribozyme primers (end-labelled) as probes, is cloned as a NotI fragment, in the anti-sense orientation, into pWP80, pWP83, pWP88 and pDIH12. The chimeric A3, CaMV 35S, A9 and A6 promoter-callase ribozyme genes are transferred to pBin19 as described for the plasmids in Example 6. The chimeric genes are transferred to pBin19 and transformed into *N. tabacum, B. napus* and *H. vulgare*. The transgenic plants are male-sterile.

EXAMPLE 9
Restoration of fertility of the plants described in Example 8

Crossing the male sterile plants with homozygous transgenic plants expressing (from the A3, A6, A9 or CaMV 35S promoters) a ribozyme that cleaves a GUC sequence in the callase(mRNA)-specific ribozyme, results in progeny that are male fertile. The target GUC sequence for the restorer-ribozyme is located such that cleavage destabilises the target mRNA by either the removal of the CAP or the polyadenylation signal. This rapidly reduces the concentration of callase(mRNA)-specific ribozyme in the cytoplasm and results in fertility restoration. This restorer-ribozyme is constructed from plasmid A6 in a similar way to that described in Example 8.

We claim:

1. Isolated DNA encoding a Brassicaceae anther specific callase enzyme, wherein said callase enzyme has the enzyme activity associated with the dissolution of the callose coat surrounding the microspores.

2. An isolated DNA encoding an anther specific callase enzyme that dissolves the callose coat surrounding the microspores, hybridizing under stringent conditions to the DNA of claim 1.

3. Isolated DNA encoding an anther specific callase enzyme that dissolves the callose coat surrounding the microspores, hybridizing under stringent conditions to a DNA encoding 53 kDa callase enzyme of Brassica napus.

4. Isolated DNA encoding an anther specific callase enzyme that dissolves the callose coat surrounding the microspores, hybridizing under stringent conditions to DNA encoding a 53.7 KDa callase enzyme of Arabidopsis thaliana.

5. Isolated DNA encoding an anther specific callase enzyme that dissolves the callose coat surrounding the microspores, hybridizing under stringent conditions to 15 to 20 nucleotides of the sequence listing of FIG. 1, SEQ ID NO. 11.

6. Isolated DNA encoding an anther specific callase enzyme that dissolves the callose coat surrounding the microspores, hybridizing under stringent conditions to 15 to 20 nucleotides of the sequence listing of FIG. 4, SEQ ID NO. 19.

7. A DNA construct comprising in a 5' to 3' direction of transcription a promoter operatively linked to DNA encoding an specific callase enzyme hybridizing the callose coat surrounding the microspores, said DNA hybridizing under stringent conditions to DNA encoding a 53 kDa callase enzyme of Brassica napus or to DNA encoding a 53.7 KDa callase enzyme of Arabidopsis thaliana, and a 3' transcription termination regulatory region.

8. The DNA construct of claim 7, wherein said promoter is tapetum-specific.

9. The DNA construct of claim 8, wherein said promoter is a Brassicaceae A3 or A9 promoter.

10. A DNA construct comprising in a 5' to 3' direction of transcription a tapetum-specific promoter operatively linked to DNA encoding an anther specific callase enzyme that dissolves the callose coat surrounding the microspores, said DNA hybridizing under stringent conditions to DNA encoding a 53 kDa callase enzyme of Brassica napus or to DNA encoding a 53.7 kDa callase enzyme of Arabidopsis thaliana, and a 3' transcription termination regulatory region derived from the cauliflower mosaic virus (CaMV) 35S gene.

11. The DNA construct of claim 10, wherein said promoter is a Brassicaceae A3 or A9 promoter.

12. The DNA construct of claim 7 or 10, wherein said construct further comprises one or more selectable markers.

13. The DNA construct of claim 12, wherein said marker sequence distinguishes a plant cell transformed with said construct from a plant cell that is not so transformed.

14. The DNA construct of claim 13, wherein said marker sequence confers antibiotic or herbicide resistance.

15. The DNA construct of claim 13, wherein said marker sequence codes for Beta 1,3-glucuronidase.

16. The DNA construct of claim 12, wherein said selectable marker is under the control of a second, non tapetum-specific promoter.

17. The DNA construct of claim 16, wherein said second promoter is derived from the cauliflower mosaic virus (CaMV) 35S gene.

18. A plant cell transformed with the DNA construct of claim 7 or 10.

19. A plant or a part of a plant each comprising plant cells transformed with the DNA construct of claim 7 or 10.

20. A transgenic seed from said plant of claim 19.

* * * * *

UNITED STATES PATENT AND TRADEMARK OFFICE
CERTIFICATE OF CORRECTION

PATENT NO   : 5,955,653
DATED       : September 21,1999
INVENTOR(S) : Roderick John Scott; John Draper; Wyatt Paul It is certified that error appears in the above-identified patent and that said Letters Patent is hereby corrected as shown below:

In claim 7, line 3, before "specific" insert --anther--

In claim 7, line 3, delete "hydrizing" and insert --that dissolves--

Signed and Sealed this

Twenty-second Day of August, 2000

Attest:

Q. TODD DICKINSON

*Attesting Officer*     *Director of Patents and Trademarks*

SEQUENCE LISTING (1) GENERAL INFORMATION:

(iii) NUMBER OF SEQUENCES: 24

(2) INFORMATION FOR SEQ ID NO: 1:

(i) SEQUENCE CHARACTERISTICS:
      (A) LENGTH: 42 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: misc_feature
      (B) LOCATION: 1..42
      (D) OTHER INFORMATION: /product= "EXAMPLE 3A PRIMER"

(xi) SEQUENCE DESCRIPTION: SEQ ID NO: 1:

```
GGGTCTAGAC CATGGGCACA GGTTATCAAC ACGTTTGACG GG                          42
```

(2) INFORMATION FOR SEQ ID NO: 2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..20
        (D) OTHER INFORMATION: /product= "EXAMPLE 3A PRIMER"

(xi) SEQUENCE DESCRIPTION: SEQ ID NO: 2:

```
GTAAAACGAC GGCCAGTGCC                                                  20
```

(2) INFORMATION FOR SEQ ID NO: 3:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..29
        (D) OTHER INFORMATION: /product= "EXAMPLE 3B PRIMER"

(xi) SEQUENCE DESCRIPTION: SEQ ID NO: 3:

```
GGGACTAGTC CATGGGTTTG CCCAAATCC                                        29
```

(2) INFORMATION FOR SEQ ID NO: 4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..17
        (D) OTHER INFORMATION: /product= "EXAMPLE 3B PRIMER"

(xi) SEQUENCE DESCRIPTION: SEQ ID NO: 4:

```
AATACGACTC ACTATAG                                                     17
```

(2) INFORMATION FOR SEQ ID NO: 5:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..36
        (D) OTHER INFORMATION: /product= "EXAMPLE 4A PRIMER"

(xi) SEQUENCE DESCRIPTION: SEQ ID NO: 5:

```
GGGACTAGTG TCACGCTGAC AAAGACATGT CTCTTC                              36
```

(2) INFORMATION FOR SEQ ID NO: 6:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..34
        (D) OTHER INFORMATION: /product= "EXAMPLE 4A PRIMER"

(xi) SEQUENCE DESCRIPTION: SEQ ID NO: 6:

```
CCCCGCGGTC ACAGAGTAAC GCTCGGAAAC TTGC                                34
```

(2) INFORMATION FOR SEQ ID NO: 7:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..36
        (D) OTHER INFORMATION: /product= "EXAMPLE 4B PRIMER"

(xi) SEQUENCE DESCRIPTION: SEQ ID NO: 7:

```
GGGACTAGTG TCACGCTGAC AAAGACATGT CTCTTC                              36
```

(2) INFORMATION FOR SEQ ID NO: 8:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..31
        (D) OTHER INFORMATION: /product= "EXAMPLE 4B PRIMER"

(xi) SEQUENCE DESCRIPTION: SEQ ID NO: 8:

```
CCCCGCGGTT AGAAATCTAC GTGTAGATTG G                                   31
```

(2) INFORMATION FOR SEQ ID NO: 9:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..52
        (D) OTHER INFORMATION: /product= "EXAMPLE 8 PRIMER"

(xi) SEQUENCE DESCRIPTION: SEQ ID NO: 9:

```
CGGCGTCGTA GAGCTTCTGA AGATGGCCCG GTAGGGCCGA AACATGACCG GC          52
```

(2) INFORMATION FOR SEQ ID NO: 10:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: misc_feature
        (B) LOCATION: 1..51
        (D) OTHER INFORMATION: /product= "EXAMPLE 8 PRIMER"

(xi) SEQUENCE DESCRIPTION: SEQ ID NO: 10:

```
CGTTGGCTCC TTCCTGAAGA TGGCCCGGTA GGGCCGAAAC CGGTACGCAC C           51
```

(2) INFORMATION FOR SEQ ID NO: 11:

(i) SEQUENCE CHARACTERISTICS:
        (A) LENGTH: 1532 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Brassica napus (ix) FEATURE:
        (A) NAME/KEY: CDS
        (B) LOCATION: 3..1424
        (D) OTHER INFORMATION: /product= "DEDUCED PROTEIN SEQUENCE
            OF ORF IN A6 OF B. NAPUS"

(xi) SEQUENCE DESCRIPTION: SEQ ID NO: 11:

```
CT TTC TTC CTC TTC ACC CTC GTC GTC TTT TCA AGT ACA AGT TGC TCA     47
   Phe Phe Leu Phe Thr Leu Val Val Phe Ser Ser Thr Ser Cys Ser
    1               5                  10                  15

GCG GTT GGG TTC CAA CAT CCG CAC AGG TAT ATA CAG AAA AAA ACG ATG    95
Ala Val Gly Phe Gln His Pro His Arg Tyr Ile Gln Lys Lys Thr Met
             20                  25                  30

CTA GAG TTA GCC AGC AAG ATT GGT ATT AAC TAT GGT AGA CAA GGA AAC    143
Leu Glu Leu Ala Ser Lys Ile Gly Ile Asn Tyr Gly Arg Gln Gly Asn
                 35                  40                  45

AAC CTA CCA TCT CCT TAC CAA TCG ATC AAT TTC ATC AAA CTC ATC AAA    191
Asn Leu Pro Ser Pro Tyr Gln Ser Ile Asn Phe Ile Lys Leu Ile Lys
         50                  55                  60

GCC GGT CAT GTC AAG CTC TAC GAC GCC GAT CCA GAG AGT CTA ACA CTC    239
Ala Gly His Val Lys Leu Tyr Asp Ala Asp Pro Glu Ser Leu Thr Leu
     65                  70                  75

CTC TCT CAA ACC AAT CTC TAC GTC ACC ATA GCG GTG CCA ACC CAC CAG    287
Leu Ser Gln Thr Asn Leu Tyr Val Thr Ile Ala Val Pro Thr His Gln
 80                  85                  90                  95

ATC ACT TCC CTC AGC GCC AAC CAA ACT ACA GCT GAA GAT TGG GTC AAA    335
Ile Thr Ser Leu Ser Ala Asn Gln Thr Thr Ala Glu Asp Trp Val Lys
                100                 105                 110

ACC AAT ATC CTC CCT TAC TAC CCA CAA ACA CAA ATA CGA TTT GTC CTT    383
Thr Asn Ile Leu Pro Tyr Tyr Pro Gln Thr Gln Ile Arg Phe Val Leu
            115                 120                 125

GTT GGA AAC GAA ATC CTC TCC GTC AAA GAT AGG AAC ATA ACC GGC AAT    431
Val Gly Asn Glu Ile Leu Ser Val Lys Asp Arg Asn Ile Thr Gly Asn
        130                 135                 140
```

```
GTC GTA CCG GCA ATG CGA AAA ATC GTG AAC TCT CTC AGA GCC CAT GGG      479
Val Val Pro Ala Met Arg Lys Ile Val Asn Ser Leu Arg Ala His Gly
    145                 150                 155

ATT CAC AAC ATC AAA GTC GGT ACA CCT TTA GCT ATG GAT TCT CTT CGA      527
Ile His Asn Ile Lys Val Gly Thr Pro Leu Ala Met Asp Ser Leu Arg
160                 165                 170                 175

TCA ACG TTT CCG CCG TCG AAC TCA ACA TTC CGG GGA GAT ATC GCC TTA      575
Ser Thr Phe Pro Pro Ser Asn Ser Thr Phe Arg Gly Asp Ile Ala Leu
                180                 185                 190

CCG TTA ATG TTG CCG TTG CTG AAG TTT CTC AAC GGA ACA AAC TCT TAC      623
Pro Leu Met Leu Pro Leu Leu Lys Phe Leu Asn Gly Thr Asn Ser Tyr
                195                 200                 205

TTC TTT ATC AAT CTT CAA CCT TAC TTC CGT TGG TCA AGA AAC CCT AAT      671
Phe Phe Ile Asn Leu Gln Pro Tyr Phe Arg Trp Ser Arg Asn Pro Asn
        210                 215                 220

CAC ACC ACG TTG GAT TTC GCT CTG TTT CAA GGA AAC TCA ACT TAT ACC      719
His Thr Thr Leu Asp Phe Ala Leu Phe Gln Gly Asn Ser Thr Tyr Thr
        225                 230                 235

GAT CCT CAT ACC GGT TTG GTT TAC CAT AAT CTT GTA GAC CAA ATG TTG      767
Asp Pro His Thr Gly Leu Val Tyr His Asn Leu Val Asp Gln Met Leu
240                 245                 250                 255

GAT TCG GTT ATC TTC GCC ATG ACC AAG CTC GGT TAT CCA TAC ATC CGT      815
Asp Ser Val Ile Phe Ala Met Thr Lys Leu Gly Tyr Pro Tyr Ile Arg
                260                 265                 270

ATC GCA ATC TCT GAA ACC GGA TGG CCT AAC TCC GGC GAC ATC GAC GAA      863
Ile Ala Ile Ser Glu Thr Gly Trp Pro Asn Ser Gly Asp Ile Asp Glu
                275                 280                 285

ATC GGA GCT AAC GTT TTC AAC GCC GCC ACG TAT AAC CGG AAT TTG ATC      911
Ile Gly Ala Asn Val Phe Asn Ala Ala Thr Tyr Asn Arg Asn Leu Ile
                290                 295                 300

AAG AAG ATG ACC GCA ACT CCA CCA ATC GGT ACA CCA GCT AGA CCC GGT      959
Lys Lys Met Thr Ala Thr Pro Pro Ile Gly Thr Pro Ala Arg Pro Gly
305                 310                 315

TCA CCT ATA CCG ACA TTT GTT TTC TCC TTA TTT AAC GAA AAC AAG AAA     1007
Ser Pro Ile Pro Thr Phe Val Phe Ser Leu Phe Asn Glu Asn Lys Lys
320                 325                 330                 335

CCC GGT TCG GGA ACA CAA AGA CAT TGG GGA ATC TTG CAT CCG GAC GGT     1055
Pro Gly Ser Gly Thr Gln Arg His Trp Gly Ile Leu His Pro Asp Gly
                340                 345                 350

ACA CCA ATC TAC GAC ATT GAT TTT ACC GGT CAA AAA CCC TTA ACC GGT     1103
Thr Pro Ile Tyr Asp Ile Asp Phe Thr Gly Gln Lys Pro Leu Thr Gly
                355                 360                 365

TTT AAC CCT CTG CCT AAA CCG ACG AAT AAC GTT CCT TAC AAG GGT CAA     1151
Phe Asn Pro Leu Pro Lys Pro Thr Asn Asn Val Pro Tyr Lys Gly Gln
                370                 375                 380

GTG TGG TGC GTA CCG GTC GAA GGA GCC AAC GAG ACT GAG CTC GAG GAA     1199
Val Trp Cys Val Pro Val Glu Gly Ala Asn Glu Thr Glu Leu Glu Glu
385                 390                 395

GCT TTG AGG ATG GCT TGT GCC CGA AGC AAC ACG ACG TGT GCG GCT TTG     1247
Ala Leu Arg Met Ala Cys Ala Arg Ser Asn Thr Thr Cys Ala Ala Leu
400                 405                 410                 415

GTT CCT GGC AGA GAA TGT TAC GAG CCG GTC TCT GTT TAT TGG CAC GCA     1295
Val Pro Gly Arg Glu Cys Tyr Glu Pro Val Ser Val Tyr Trp His Ala
                420                 425                 430

AGC TAC GCG CTT AAC TCG TAC TGG GCA CAG TTC CGT AGC CAA AAC GTC     1343
Ser Tyr Ala Leu Asn Ser Tyr Trp Ala Gln Phe Arg Ser Gln Asn Val
                435                 440                 445

CAA TGT TAC TTC AAT GGA TTA GCT CAT GAG ACC ACG ACT AAC CCT GGA     1391
Gln Cys Tyr Phe Asn Gly Leu Ala His Glu Thr Thr Thr Asn Pro Gly
                450                 455                 460
```

```
AAT GAT CGC TGC AAG TTT CCG AGC GTT ACT CTG TGAGGAAGAA CGCCTGAAAG       1444
Asn Asp Arg Cys Lys Phe Pro Ser Val Thr Leu
465                     470

AGATTTAAGA TGATCAAAGC TGGATTATTC GTATTTACTC ATTCTAGATT TTCTGGTTTC       1504

TGTTTCGTGT GGCCTAATGT TGAGAAAA                                          1532

(2) INFORMATION FOR SEQ ID NO: 12:

(i) SEQUENCE CHARACTERISTICS:
        (A) LENGTH: 474 amino acids
        (B) TYPE: amino acid
        (D) TOPOLOGY: linear (ii) MOLECULE TYPE: protein (xi) SEQUENCE DESCRIPTION: SEQ ID NO: 12:

Phe Phe Leu Phe Thr Leu Val Val Phe Ser Ser Thr Ser Cys Ser Ala
1               5                   10                  15

Val Gly Phe Gln His Pro His Arg Tyr Ile Gln Lys Lys Thr Met Leu
            20                  25                  30

Glu Leu Ala Ser Lys Ile Gly Ile Asn Tyr Gly Arg Gln Gly Asn Asn
        35                  40                  45

Leu Pro Ser Pro Tyr Gln Ser Ile Asn Phe Ile Lys Leu Ile Lys Ala
    50                  55                  60

Gly His Val Lys Leu Tyr Asp Ala Asp Pro Glu Ser Leu Thr Leu Leu
65                  70                  75                  80

Ser Gln Thr Asn Leu Tyr Val Thr Ile Ala Val Pro Thr His Gln Ile
                85                  90                  95

Thr Ser Leu Ser Ala Asn Gln Thr Thr Ala Glu Asp Trp Val Lys Thr
            100                 105                 110

Asn Ile Leu Pro Tyr Tyr Pro Gln Thr Gln Ile Arg Phe Val Leu Val
        115                 120                 125

Gly Asn Glu Ile Leu Ser Val Lys Asp Arg Asn Ile Thr Gly Asn Val
    130                 135                 140

Val Pro Ala Met Arg Lys Ile Val Asn Ser Leu Arg Ala His Gly Ile
145                 150                 155                 160

His Asn Ile Lys Val Gly Thr Pro Leu Ala Met Asp Ser Leu Arg Ser
                165                 170                 175

Thr Phe Pro Pro Ser Asn Ser Thr Phe Arg Gly Asp Ile Ala Leu Pro
            180                 185                 190

Leu Met Leu Pro Leu Leu Lys Phe Leu Asn Gly Thr Asn Ser Tyr Phe
        195                 200                 205

Phe Ile Asn Leu Gln Pro Tyr Phe Arg Trp Ser Arg Asn Pro Asn His
    210                 215                 220

Thr Thr Leu Asp Phe Ala Leu Phe Gln Gly Asn Ser Thr Tyr Thr Asp
225                 230                 235                 240

Pro His Thr Gly Leu Val Tyr His Asn Leu Val Asp Gln Met Leu Asp
                245                 250                 255

Ser Val Ile Phe Ala Met Thr Lys Leu Gly Tyr Pro Tyr Ile Arg Ile
            260                 265                 270

Ala Ile Ser Glu Thr Gly Trp Pro Asn Ser Gly Asp Ile Asp Glu Ile
        275                 280                 285

Gly Ala Asn Val Phe Asn Ala Ala Thr Tyr Asn Arg Asn Leu Ile Lys
    290                 295                 300

Lys Met Thr Ala Thr Pro Pro Ile Gly Thr Pro Ala Arg Pro Gly Ser
305                 310                 315                 320
```

```
Pro Ile Pro Thr Phe Val Phe Ser Leu Phe Asn Glu Asn Lys Lys Pro
                325                 330                 335

Gly Ser Gly Thr Gln Arg His Trp Gly Ile Leu His Pro Asp Gly Thr
            340                 345                 350

Pro Ile Tyr Asp Ile Asp Phe Thr Gly Gln Lys Pro Leu Thr Gly Phe
            355                 360                 365

Asn Pro Leu Pro Lys Pro Thr Asn Asn Val Pro Tyr Lys Gly Gln Val
            370                 375                 380

Trp Cys Val Pro Val Glu Gly Ala Asn Glu Thr Glu Leu Glu Glu Ala
385                 390                 395                 400

Leu Arg Met Ala Cys Ala Arg Ser Asn Thr Thr Cys Ala Ala Leu Val
                405                 410                 415

Pro Gly Arg Glu Cys Tyr Glu Pro Val Ser Val Tyr Trp His Ala Ser
                420                 425                 430

Tyr Ala Leu Asn Ser Tyr Trp Ala Gln Phe Arg Ser Gln Asn Val Gln
                435                 440                 445

Cys Tyr Phe Asn Gly Leu Ala His Glu Thr Thr Thr Asn Pro Gly Asn
                450                 455                 460

Asp Arg Cys Lys Phe Pro Ser Val Thr Leu
465                 470
```

(2) INFORMATION FOR SEQ ID NO: 13:

(i) SEQUENCE CHARACTERISTICS:
        (A) LENGTH: 362 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: TOBACCO GLUCANASE NPGLUC (xi) SEQUENCE DESCRIPTION: SEQ ID NO: 13:

```
Ala Leu Gln Met Ala Ala Ile Ile Leu Leu Gly Leu Leu Val Ser Ser
1               5                   10                  15

Thr Glu Ile Val Gly Ala Gln Ser Val Gly Val Cys Tyr Gly Met Leu
                20                  25                  30

Gly Asn Asn Leu Pro Pro Ala Ser Gln Val Val Gln Leu Tyr Lys Ser
            35                  40                  45

Lys Asn Ile Arg Arg Met Arg Leu Tyr Asp Pro Asn Gln Ala Ala Leu
    50                  55                  60

Gln Ala Leu Arg Gly Ser Asn Ile Glu Val Met Leu Gly Val Pro Asn
65                  70                  75                  80

Ser Asp Leu Gln Asn Ile Ala Ala Asn Pro Ser Asn Ala Asn Asn Trp
                85                  90                  95

Val Gln Arg Asn Val Arg Asn Phe Trp Pro Ala Val Lys Phe Arg Tyr
                100                 105                 110

Ile Ala Val Gly Asn Glu Val Ser Pro Val Thr Gly Thr Ser Ser Leu
                115                 120                 125

Thr Arg Tyr Leu Leu Pro Ala Met Arg Asn Ile Arg Asn Ala Ile Ser
            130                 135                 140

Ser Ala Gly Leu Gln Asn Asn Ile Lys Val Ser Ser Ser Val Asp Met
145                 150                 155                 160

Thr Leu Ile Gly Asn Ser Phe Pro Pro Ser Gln Gly Ser Phe Arg Asn
                165                 170                 175
```

```
Asp Val Arg Ser Phe Ile Asp Pro Ile Ile Gly Phe Val Arg Arg Ile
            180                 185                 190

Asn Ser Pro Leu Leu Val Asn Ile Tyr Pro Tyr Phe Ser Tyr Ala Gly
        195                 200                 205

Asn Pro Arg Asp Ile Ser Leu Pro Tyr Ala Leu Phe Thr Ala Pro Asn
        210                 215                 220

Val Val Val Gln Asp Gly Ser Leu Gly Tyr Arg Asn Leu Phe Asp Ala
225                 230                 235                 240

Met Ser Asp Ala Val Tyr Ala Ala Leu Ser Arg Ala Gly Gly Gly Ser
                245                 250                 255

Ile Glu Ile Val Val Ser Glu Ser Gly Trp Pro Ser Ala Gly Ala Phe
                260                 265                 270

Ala Ala Thr Thr Asn Asn Ala Ala Thr Tyr Tyr Lys Asn Leu Ile Gln
            275                 280                 285

His Val Lys Arg Gly Ser Pro Arg Arg Pro Asn Lys Val Ile Glu Thr
        290                 295                 300

Tyr Leu Phe Ala Met Phe Asp Glu Asn Asn Lys Asn Pro Glu Leu Glu
305                 310                 315                 320

Lys His Phe Gly Leu Phe Ser Pro Asn Lys Gln Pro Lys Tyr Pro Leu
                325                 330                 335

Ser Phe Gly Phe Ser Asp Arg Tyr Trp Asp Ile Ser Ala Glu Asn Asn
                340                 345                 350

Ala Thr Ala Ala Ser Leu Ile Ser Glu Met
            355                 360

(2) INFORMATION FOR SEQ ID NO: 14:

(i) SEQUENCE CHARACTERISTICS:
        (A) LENGTH: 348 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: BEAN GLUCANASE (xi) SEQUENCE DESCRIPTION: SEQ ID NO: 14:

Gln Ile Gly Val Cys Tyr Gly Met Met Gly Asn Asn Leu Pro Ser Ala
1               5                   10                  15

Asn Glu Val Ile Asn Leu Tyr Arg Ser Asn Asn Ile Arg Arg Met Arg
                20                  25                  30

Leu Tyr Asp Pro Asn Gly Ala Ala Leu Gly Ala Leu Arg Asn Ser Gly
            35                  40                  45

Ile Glu Leu Ile Leu Gly Val Pro Asn Ser Asp Leu Gln Gly Leu Ala
50                  55                  60

Thr Asn Ala Asp Thr Ala Arg Gln Trp Val Gln Arg Asn Val Leu Asn
65                  70                  75                  80

Phe Trp Pro Ser Val Lys Ile Lys Tyr Ile Ala Val Gly Asn Glu Val
                85                  90                  95

Ser Pro Val Gly Gly Ser Ser Trp Tyr Ala Gln Tyr Val Leu Pro Ala
            100                 105                 110

Val Gln Asn Val Tyr Gly Ala Val Arg Ala Gln Gly Leu His Asp Gly
        115                 120                 125

Ile Lys Val Ser Thr Ala Ile Asp Met Thr Leu Ile Gly Asn Ser Tyr
        130                 135                 140

Pro Pro Ser Gln Gly Ser Phe Arg Gly Asp Val Arg Ser Tyr Leu Asp
```

```
145                 150                 155                 160
Pro Ile Ile Gly Tyr Leu Leu Tyr Ala Ser Ala Pro Leu His Val Asn
                165                 170                 175

Val Tyr Pro Tyr Phe Ser Tyr Ser Gly Asn Pro Arg Asp Ile Ser Leu
                180                 185                 190

Pro Tyr Ala Leu Phe Thr Ser Pro Asn Val Val Arg Asp Gly Gln
                195                 200                 205

Tyr Gly Tyr Gln Asn Leu Phe Asp Ala Met Leu Asp Ser Val His Ala
                210                 215                 220

Ala Ile Asp Asn Thr Arg Ile Gly Tyr Val Glu Val Val Ser Glu
225                 230                 235                 240

Ser Gly Trp Pro Ser Asp Gly Gly Phe Gly Ala Thr Tyr Asp Asn Ala
                245                 250                 255

Arg Val Tyr Leu Asp Asn Leu Val Arg Arg Ala Gly Arg Gly Ser Pro
                260                 265                 270

Arg Arg Pro Ser Lys Pro Thr Glu Thr Tyr Ile Phe Ala Met Phe Asp
                275                 280                 285

Glu Asn Gln Lys Ser Pro Glu Ile Glu Lys His Phe Gly Leu Phe Lys
                290                 295                 300

Pro Ser Lys Glu Lys Lys Tyr Pro Phe Gly Phe Gly Ala Gln Arg Met
305                 310                 315                 320

Gln Arg Leu Leu Leu Met Ser Ser Met Gln His Ile Pro Leu Arg Val
                325                 330                 335

Thr Cys Lys Leu Glu Pro Ser Ser Gln Ser Leu Leu
                340                 345

(2) INFORMATION FOR SEQ ID NO: 15:

(i) SEQUENCE CHARACTERISTICS:
        (A) LENGTH: 346 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: TOBACCO GLUCANASE PR-Q (xi) SEQUENCE DESCRIPTION: SEQ ID NO: 15:

Gln Phe Leu Phe Ser Leu Gln Met Ala His Leu Ile Val Thr Leu Leu
1               5                   10                  15

Leu Leu Ser Val Leu Thr Leu Ala Thr Leu Asp Phe Thr Gly Ala Gln
                20                  25                  30

Ala Gly Val Cys Tyr Gly Arg Gln Gly Asn Gly Leu Pro Ser Pro Ala
                35                  40                  45

Asp Val Val Ser Leu Cys Asn Arg Asn Asn Ile Arg Arg Met Arg Ile
50                  55                  60

Tyr Asp Pro Asp Gln Pro Thr Leu Glu Ala Leu Arg Gly Ser Asn Ile
65                  70                  75                  80

Glu Leu Met Leu Gly Val Pro Asn Pro Asp Leu Glu Asn Val Ala Ala
                85                  90                  95

Ser Gln Ala Asn Ala Asp Thr Trp Val Gln Asn Asn Val Arg Asn Tyr
                100                 105                 110

Gly Asn Val Lys Phe Arg Tyr Ile Ala Val Gly Asn Glu Val Ser Pro
                115                 120                 125

Leu Asn Glu Asn Ser Lys Tyr Val Pro Val Leu Leu Asn Ala Met Arg
                130                 135                 140
```

```
Asn Ile Gln Thr Ala Ile Ser Gly Ala Gly Leu Gly Asn Gln Ile Lys
145                 150                 155                 160

Val Ser Thr Ala Ile Glu Thr Gly Leu Thr Thr Asp Thr Ser Pro Pro
                165                 170                 175

Ser Asn Gly Arg Phe Lys Asp Asp Val Arg Gln Phe Ile Glu Pro Ile
            180                 185                 190

Ile Asn Phe Leu Val Thr Asn Arg Ala Pro Leu Leu Val Asn Leu Tyr
        195                 200                 205

Pro Tyr Phe Ala Ile Ala Asn Asn Ala Asp Ile Lys Leu Glu Tyr Ala
    210                 215                 220

Leu Phe Thr Ser Ser Glu Val Val Asn Asp Asn Gly Arg Gly Tyr
225                 230                 235                 240

Arg Asn Leu Phe Asp Ala Ile Leu Asp Ala Thr Tyr Ser Ala Leu Glu
                245                 250                 255

Lys Ala Ser Gly Ser Ser Leu Glu Ile Val Val Ser Glu Ser Gly Trp
            260                 265                 270

Pro Ser Ala Gly Ala Gly Gln Leu Thr Ser Ile Asp Asn Ala Arg Thr
        275                 280                 285

Tyr Asn Asn Asn Leu Ile Ser His Val Lys Gly Gly Ser Pro Lys Arg
    290                 295                 300

Pro Ser Gly Pro Ile Glu Thr Tyr Val Phe Ala Leu Phe Asp Glu Asp
305                 310                 315                 320

Gln Lys Asp Pro Glu Ile Glu Lys His Phe Gly Leu Phe Ser Ala Asn
                325                 330                 335

Met Gln Pro Lys Tyr Gln Ile Ser Phe Asn
                340                 345
```

(2) INFORMATION FOR SEQ ID NO: 16:

(i) SEQUENCE CHARACTERISTICS:
        (A) LENGTH: 334 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: BARLEY GLUCANSE (xi) SEQUENCE DESCRIPTION: SEQ ID NO: 16:

```
Met Ala Arg Lys Asp Val Ala Ser Met Phe Ala Ala Leu Phe Ile
1               5                   10                  15

Gly Ala Phe Ala Ala Val Pro Thr Ser Val Gln Ser Ile Gly Val Cys
                20                  25                  30

Tyr Gly Val Ile Gly Asn Asn Leu Pro Ser Arg Ser Asp Val Val Gln
            35                  40                  45

Leu Tyr Arg Ser Lys Gly Ile Asn Gly Met Arg Ile Tyr Phe Ala Asp
50                  55                  60

Gly Gln Ala Leu Ser Ala Leu Arg Asn Ser Gly Ile Gly Leu Ile Leu
65                  70                  75                  80

Asp Ile Gly Asn Asp Gln Leu Ala Asn Ile Ala Ala Ser Thr Ser Asn
                85                  90                  95

Ala Ala Ser Trp Val Gln Asn Asn Val Arg Pro Tyr Tyr Pro Ala Val
            100                 105                 110

Asn Ile Lys Tyr Ile Ala Ala Gly Asn Glu Val Gln Gly Gly Ala Thr
        115                 120                 125
```

-continued

```
Gln Ser Ile Leu Pro Ala Met Arg Asn Leu Asn Ala Ala Leu Ser Ala
        130                 135                 140

Ala Gly Leu Gly Ala Ile Lys Val Ser Thr Ser Ile Arg Phe Asp Glu
145                 150                 155                 160

Val Ala Asn Ser Phe Pro Pro Ser Ala Gly Val Phe Lys Asn Ala Tyr
                165                 170                 175

Met Thr Asp Val Ala Arg Leu Leu Ala Ser Thr Gly Ala Pro Leu Leu
                180                 185                 190

Ala Asn Val Tyr Pro Tyr Phe Ala Tyr Arg Asp Asn Pro Gly Ser Ile
                195                 200                 205

Ser Leu Asn Tyr Ala Thr Phe Gln Pro Gly Thr Thr Val Arg Asp Gln
        210                 215                 220

Asn Asn Gly Leu Thr Tyr Thr Ser Leu Phe Asp Ala Met Val Asp Ala
225                 230                 235                 240

Val Tyr Ala Ala Leu Glu Lys Ala Gly Ala Pro Ala Val Lys Val Val
                245                 250                 255

Val Ser Glu Ser Gly Trp Pro Ser Ala Gly Gly Phe Ala Ala Ser Ala
                260                 265                 270

Gly Asn Ala Arg Thr Tyr Asn Gln Gly Leu Ile Asn His Val Gly Gly
                275                 280                 285

Gly Thr Pro Lys Lys Arg Glu Ala Leu Glu Thr Tyr Ile Phe Ala Met
290                 295                 300

Phe Asn Glu Asn Gln Lys Thr Gly Asp Ala Thr Glu Arg Ser Phe Gly
305                 310                 315                 320

Leu Phe Asn Pro Asp Lys Ser Pro Ala Tyr Asn Ile Gln Phe
                325                 330
```

(2) INFORMATION FOR SEQ ID NO: 17:

(i) SEQUENCE CHARACTERISTICS:
        (A) LENGTH: 478 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Arabidopsis thaliana G62 GLUCANSE (xi) SEQUENCE DESCRIPTION: SEQ ID NO: 17:

```
Met Ser Leu Leu Ala Phe Phe Leu Phe Thr Ile Leu Val Phe Ser Ser
1               5                   10                  15

Ser Cys Cys Ser Ala Thr Arg Phe Gln Gly His Arg Tyr Met Gln Arg
            20                  25                  30

Lys Thr Met Leu Asp Leu Ala Ser Lys Ile Gly Ile Asn Tyr Gly Arg
        35                  40                  45

Arg Gly Asn Asn Leu Pro Ser Pro Tyr Gln Ser Ile Asn Phe Ile Lys
    50                  55                  60

Ser Ile Lys Ala Gly His Val Lys Leu Tyr Asp Ala Asp Pro Glu Ser
65                  70                  75                  80

Leu Thr Leu Leu Ser Gln Thr Asn Leu Tyr Val Thr Ile Thr Val Pro
                85                  90                  95

Asn His Gln Ile Thr Ala Leu Ser Ser Asn Gln Thr Ile Ala Asp Glu
                100                 105                 110

Trp Val Arg Thr Asn Ile Leu Pro Tyr Tyr Pro Gln Thr Gln Ile Arg
                115                 120                 125

Phe Val Leu Val Gly Asn Glu Ile Leu Ser Tyr Asn Ser Gly Asn Val
```

```
            130                 135                 140
Ser Val Asn Leu Val Pro Ala Met Arg Lys Ile Val Asn Ser Leu Arg
145                 150                 155                 160

Leu His Gly Ile His Asn Ile Lys Val Gly Thr Pro Leu Ala Met Asp
                165                 170                 175

Ser Leu Arg Ser Ser Phe Pro Arg Ser Asn Gly Thr Phe Arg Glu Glu
            180                 185                 190

Ile Thr Gly Pro Val Met Leu Pro Leu Lys Phe Leu Asn Gly Thr
        195                 200                 205

Asn Ser Tyr Phe Phe Leu Asn Val His Pro Tyr Phe Arg Trp Ser Arg
210                 215                 220

Asn Pro Met Asn Thr Ser Leu Asp Phe Ala Leu Phe Gln Gly His Ser
225                 230                 235                 240

Thr Tyr Thr Asp Pro Gln Thr Gly Leu Val Tyr Arg Asn Leu Leu Asp
                245                 250                 255

Gln Met Leu Asp Ser Val Leu Phe Ala Met Thr Lys Leu Gly Tyr Pro
            260                 265                 270

His Met Arg Leu Ala Ile Ser Glu Thr Gly Trp Pro Asn Phe Gly Asp
            275                 280                 285

Ile Asp Glu Thr Gly Ala Asn Ile Leu Asn Ala Ala Thr Tyr Asn Arg
290                 295                 300

Asn Leu Ile Lys Lys Met Ser Ala Ser Pro Pro Ile Gly Thr Pro Ser
305                 310                 315                 320

Arg Pro Gly Leu Pro Ile Pro Thr Phe Val Phe Ser Leu Phe Asn Glu
                325                 330                 335

Asn Gln Lys Ser Gly Ser Gly Thr Gln Arg His Trp Gly Ile Phe Asp
            340                 345                 350

Pro Asp Gly Ser Pro Ile Tyr Asp Val Asp Phe Thr Gly Gln Thr Pro
            355                 360                 365

Leu Thr Gly Phe Asn Pro Leu Pro Lys Pro Thr Asn Asn Val Pro Tyr
370                 375                 380

Lys Gly Gln Val Trp Cys Val Pro Val Glu Gly Ala Asn Glu Thr Glu
385                 390                 395                 400

Leu Glu Glu Thr Leu Arg Met Ala Cys Ala Gln Ser Asn Thr Thr Cys
                405                 410                 415

Ala Ala Leu Ala Pro Gly Arg Glu Cys Tyr Glu Pro Val Ser Ile Tyr
            420                 425                 430

Trp His Ala Ser Tyr Ala Leu Asn Ser Tyr Trp Ala Gln Phe Arg Asn
            435                 440                 445

Gln Ser Ile Gln Cys Phe Phe Asn Gly Leu Ala His Glu Thr Thr Thr
450                 455                 460

Asn Pro Gly Asn Asp Arg Cys Lys Phe Pro Ser Val Thr Leu
465                 470                 475
```

(2) INFORMATION FOR SEQ ID NO: 18:

(i) SEQUENCE CHARACTERISTICS:
        (A) LENGTH: 474 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Brassica napus A6 GLUCANASE (xi) SEQUENCE DESCRIPTION: SEQ ID NO: 18:

```
Phe Phe Leu Phe Thr Leu Val Val Phe Ser Ser Thr Ser Cys Ser Ala
1               5                   10                  15

Val Gly Phe Gln His Pro His Arg Tyr Ile Gln Lys Lys Thr Met Leu
            20                  25                  30

Glu Leu Ala Ser Lys Ile Gly Ile Asn Tyr Gly Arg Gln Gly Asn Asn
            35                  40                  45

Leu Pro Ser Pro Tyr Gln Ser Ile Asn Phe Ile Lys Leu Ile Lys Ala
    50                  55                  60

Gly His Val Lys Leu Tyr Asp Ala Asp Pro Glu Ser Leu Thr Leu Leu
65                  70                  75                  80

Ser Gln Thr Asn Leu Tyr Val Thr Ile Ala Val Pro Thr His Gln Ile
                85                  90                  95

Thr Ser Leu Ser Ala Asn Gln Thr Thr Ala Glu Asp Trp Val Lys Thr
                100                 105                 110

Asn Ile Leu Pro Tyr Tyr Pro Gln Thr Gln Ile Arg Phe Val Leu Val
            115                 120                 125

Gly Asn Glu Ile Leu Ser Val Lys Asp Arg Asn Ile Thr Gly Asn Val
    130                 135                 140

Val Pro Ala Met Arg Lys Ile Val Asn Ser Leu Arg Ala His Gly Ile
145                 150                 155                 160

His Asn Ile Lys Val Gly Thr Pro Leu Ala Met Asp Ser Leu Arg Ser
                165                 170                 175

Thr Phe Pro Pro Ser Asn Ser Thr Phe Arg Gly Asp Ile Ala Leu Pro
            180                 185                 190

Leu Met Leu Pro Leu Leu Lys Phe Leu Asn Gly Thr Asn Ser Tyr Phe
            195                 200                 205

Phe Ile Asn Leu Gln Pro Tyr Phe Arg Trp Ser Arg Asn Pro Asn His
    210                 215                 220

Thr Thr Leu Asp Phe Ala Leu Phe Gln Gly Asn Ser Tyr Thr Asp Asp
225                 230                 235                 240

Pro His Thr Gly Leu Val Tyr His Asn Leu Val Asp Gln Met Leu Asp
                245                 250                 255

Ser Val Ile Phe Ala Met Thr Lys Leu Gly Tyr Pro Tyr Ile Arg Ile
                260                 265                 270

Ala Ile Ser Glu Thr Gly Trp Pro Asn Ser Gly Asp Ile Asp Glu Ile
        275                 280                 285

Gly Ala Asn Val Phe Asn Ala Ala Thr Tyr Asn Arg Asn Leu Ile Lys
    290                 295                 300

Lys Met Thr Ala Thr Pro Pro Ile Gly Thr Pro Ala Arg Pro Gly Ser
305                 310                 315                 320

Pro Ile Pro Thr Phe Val Phe Ser Leu Phe Asn Glu Asn Lys Lys Pro
                325                 330                 335

Gly Ser Gly Thr Gln Arg His Trp Gly Ile Leu His Pro Asp Gly Thr
            340                 345                 350

Pro Ile Tyr Asp Ile Asp Phe Thr Gly Gln Lys Pro Leu Thr Gly Phe
        355                 360                 365

Asn Pro Leu Pro Lys Pro Thr Asn Val Pro Tyr Lys Gly Gln Val
    370                 375                 380

Trp Cys Val Pro Val Glu Gly Ala Asn Glu Thr Leu Glu Glu Ala
385                 390                 395                 400

Leu Arg Met Ala Cys Ala Arg Ser Asn Thr Thr Cys Ala Ala Leu Val
                405                 410                 415

Pro Gly Arg Glu Cys Tyr Glu Pro Val Ser Val Tyr Trp His Ala Ser
```

```
                420                425                430
Tyr Ala Leu Asn Ser Tyr Trp Ala Gln Phe Arg Ser Gln Asn Val Gln
            435                440                445

Cys Tyr Phe Asn Gly Leu Ala His Glu Thr Thr Thr Asn Pro Gly Asn
    450                455                460

Asp Arg Cys Lys Phe Pro Ser Val Thr Leu
465                 470
```

(2) INFORMATION FOR SEQ ID NO: 19:

(i) SEQUENCE CHARACTERISTICS:
        (A) LENGTH: 2569 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Arabidopsis thaliana A6

(ix) FEATURE:
        (A) NAME/KEY: intron
        (B) LOCATION: 928..1009

(ix) FEATURE:
        (A) NAME/KEY: intron
        (B) LOCATION: 2363..2439

(ix) FEATURE:
        (A) NAME/KEY: CDS
        (B) LOCATION: join(882..927, 1010..2362, 2440..2474)

(ix) FEATURE:
        (A) NAME/KEY: exon
        (B) LOCATION: 882..927

(ix) FEATURE:
        (A) NAME/KEY: exon
        (B) LOCATION: 1010..2362

(ix) FEATURE:
        (A) NAME/KEY: exon
        (B) LOCATION: 2440..2474

(xi) SEQUENCE DESCRIPTION: SEQ ID NO: 19:

```
GAATTCACAC AAAGCAATTA ACAAAGTTAA CCAAATCCCA AATTCGAATT TGGTTCCCTA      60

TTCTACAGCC TAACCGTATT CTGAGATCTG TAACAGAGTC ATGAACAGAA AATACCAACC     120

TCGAGCTGAC CGGAGCGGCA CGATTTTGAC TCGTCGAGCG TGTAAAAGAA GGAAGTACCA     180

TTGTTCCATT CAAGGTCGTA GGTAATACCA CCGAGCTGCT CCTGGATGAT ATTGAAATTA     240

CGACCGTTGG TCCAGTCGTA CCAAAGGTCG ATCATCGAGA GATCGCCGGA GTAATTCATG     300

AACATTAGCG CGTGGAACTG GTGTGGCCAT GGCGTCGGCA CCGGCTCATC CGCGGCGGCA     360

TTTTCACGCC GGCGGTTATA TAAATGAAGA TAACGATTAC TATGAGTGGT CGTCAAAAG     420

CCATGTGTAT CAGTGTGGTA CTGAAGTTTT GGTTCGTGCA CGGAAGATAA ATTAAAATAC     480

TATATAGTAT ACAGTTCTTT TAAATTCTAC ATAAATTGTT ATCATCGAAA CATACATTTT     540

AGTCCATTAG TCTACTAAAC TCATTATTGA TGTATAATCT CTCAATCTAC AATCAGAAAT     600

GTATTTGCAA AATTAACAAT ATTGGGGAAA GTGTTTCTTG GTTCAATTTG AACCGATCCA     660

ACCAACAATC CTTTTAAAAT CATAGCACAA AGAACTATG AGAGTTTCAA AAAGAAAATC     720

AAAAGCCAAA ACAAAGCTTT TCTTGCATGA CTCAATAAAC CTACACTACA CCATACTCTT     780

ACTTATAAAC CTCATCTCCA ATGCCACACC ATTCCATCTT AAAATCACAT TCTGATCATC     840

ACCAACACAT TGCAAACCAA ACCAGACACA AACACAAAGA C ATG TCT CTT CTT        893
```

```
                           Met Ser Leu Leu
                              1

GCT TTC TTC CTC TTC ACC ATC CTT GTC TTT TCA  A GTAAGTCATC          937
Ala Phe Phe Leu Phe Thr Ile Leu Val Phe Ser
 5                   10                  15

TTAATAATGC ATCATGTTTA CATTTTCTTT ACGTAATCTC CCATATTGAA CATGGTTTTC  997

TTGGTTTTAC AG  GT TCA TGT TGT TCC GCA ACT CGG TTC CAA GGG CAC     1044
              Ser Ser Cys Cys Ser Ala Thr Arg Phe Gln Gly His
                              20                  25

AGG TAC ATG CAG AGG AAA ACA ATG CTA GAT TTG GCT AGC AAG ATT GGT   1092
Arg Tyr Met Gln Arg Lys Thr Met Leu Asp Leu Ala Ser Lys Ile Gly
            30                  35                  40

ATC AAC TAT GGA AGA AGA GGA AAC AAC CTC CCA TCT CCA TAT CAA TCC   1140
Ile Asn Tyr Gly Arg Arg Gly Asn Asn Leu Pro Ser Pro Tyr Gln Ser
 45                  50                  55

ATC AAC TTC ATC AAA TCT ATC AAA GCT GGT CAT GTC AAG CTC TAT GAC   1188
Ile Asn Phe Ile Lys Ser Ile Lys Ala Gly His Val Lys Leu Tyr Asp
 60                  65                  70                  75

GCC GAT CCA GAG AGT CTC ACA CTC CTC TCT CAA ACC AAT CTC TAC GTC   1236
Ala Asp Pro Glu Ser Leu Thr Leu Leu Ser Gln Thr Asn Leu Tyr Val
                 80                  85                  90

ACC ATA ACC GTC CCT AAC CAC CAA ATC ACC GCC CTC AGC TCT AAC CAA   1284
Thr Ile Thr Val Pro Asn His Gln Ile Thr Ala Leu Ser Ser Asn Gln
                     95                 100                 105

ACC ATA GCT GAC GAA TGG GTC AGA ACT AAC ATC CTC CCT TAC TAT CCA   1332
Thr Ile Ala Asp Glu Trp Val Arg Thr Asn Ile Leu Pro Tyr Tyr Pro
            110                 115                 120

CAA ACA CAA ATC CGT TTT GTC CTT GTC GGA AAC GAA ATC CTC AGC TAC   1380
Gln Thr Gln Ile Arg Phe Val Leu Val Gly Asn Glu Ile Leu Ser Tyr
125                 130                 135

AAT TCT GGG AAT GTC TCT GTG AAT CTT GTA CCG GCG ATG CGC AAG ATC   1428
Asn Ser Gly Asn Val Ser Val Asn Leu Val Pro Ala Met Arg Lys Ile
140                 145                 150                 155

GTT AAC TCA CTC AGA TTA CAT GGG ATT CAC AAC ATC AAA GTT GGG ACA   1476
Val Asn Ser Leu Arg Leu His Gly Ile His Asn Ile Lys Val Gly Thr
                160                 165                 170

CCT CTA GCT ATG GAT TCT CTC CGG TCG TCG TTT CCT CGA TCG AAC GGA   1524
Pro Leu Ala Met Asp Ser Leu Arg Ser Ser Phe Pro Arg Ser Asn Gly
                175                 180                 185

ACA TTC CGG GAA GAA ATC ACC GGA CCG GTG ATG TTA CCG TTG CTG AAG   1572
Thr Phe Arg Glu Glu Ile Thr Gly Pro Val Met Leu Pro Leu Leu Lys
            190                 195                 200

TTT CTC AAC GGA ACA AAC TCT TAC TTC TTC CTT AAT GTT CAT CCT TAC   1620
Phe Leu Asn Gly Thr Asn Ser Tyr Phe Phe Leu Asn Val His Pro Tyr
205                 210                 215

TTC CGT TGG TCA AGA AAC CCC ATG AAC ACC AGT TTG GAT TTT GCT CTG   1668
Phe Arg Trp Ser Arg Asn Pro Met Asn Thr Ser Leu Asp Phe Ala Leu
220                 225                 230                 235

TTC CAA GGA CAC TCA ACC TAT ACC GAT CCT CAA ACC GGT TTG GTT TAC   1716
Phe Gln Gly His Ser Thr Tyr Thr Asp Pro Gln Thr Gly Leu Val Tyr
                240                 245                 250

CGT AAT CTT CTA GAC CAA ATG TTG GAT TCG GTT CTC TTC GCC ATG ACC   1764
Arg Asn Leu Leu Asp Gln Met Leu Asp Ser Val Leu Phe Ala Met Thr
                255                 260                 265

AAA CTC GGT TAT CCA CAT ATG CGC CTC GCG ATC TCT GAA ACC GGA TGG   1812
Lys Leu Gly Tyr Pro His Met Arg Leu Ala Ile Ser Glu Thr Gly Trp
            270                 275                 280

CCT AAT TTC GGT GAC ATC GAC GAA ACC GGA GCC AAC ATT CTC AAC GCA   1860
Pro Asn Phe Gly Asp Ile Asp Glu Thr Gly Ala Asn Ile Leu Asn Ala
285                 290                 295
```

```
GCT ACC TAT AAC CGT AAT CTG ATC AAG AAG ATG AGC GCA AGT CCT CCA         1908
Ala Thr Tyr Asn Arg Asn Leu Ile Lys Lys Met Ser Ala Ser Pro Pro
300                 305                 310                 315

ATC GGT ACA CCA TCA AGA CCC GGT TTA CCA ATA CCG ACA TTT GTT TTC         1956
Ile Gly Thr Pro Ser Arg Pro Gly Leu Pro Ile Pro Thr Phe Val Phe
                320                 325                 330

TCC TTA TTC AAC GAA AAC CAG AAA TCC GGT TCG GGG ACA CAG AGA CAT         2004
Ser Leu Phe Asn Glu Asn Gln Lys Ser Gly Ser Gly Thr Gln Arg His
            335                 340                 345

TGG GGA ATC TTC GAT CCC GAC GGT TCA CCA ATC TAC GAC GTA GAT TTC         2052
Trp Gly Ile Phe Asp Pro Asp Gly Ser Pro Ile Tyr Asp Val Asp Phe
        350                 355                 360

ACC GGT CAA ACA CCC TTA ACC GGT TTC AAC CCG TTA CCT AAA CCG ACG         2100
Thr Gly Gln Thr Pro Leu Thr Gly Phe Asn Pro Leu Pro Lys Pro Thr
    365                 370                 375

AAC AAC GTT CCT TAC AAA GGT CAA GTG TGG TGC GTA CCA GTC GAA GGA         2148
Asn Asn Val Pro Tyr Lys Gly Gln Val Trp Cys Val Pro Val Glu Gly
380                 385                 390                 395

GCC AAC GAG ACT GAG CTT GAA GAA ACA TTG AGG ATG GCT TGT GCC CAA         2196
Ala Asn Glu Thr Glu Leu Glu Glu Thr Leu Arg Met Ala Cys Ala Gln
                400                 405                 410

AGC AAC ACC ACT TGT GCA GCT TTA GCT CCT GGG AGA GAA TGT TAC GAA         2244
Ser Asn Thr Thr Cys Ala Ala Leu Ala Pro Gly Arg Glu Cys Tyr Glu
            415                 420                 425

CCA GTC TCC ATT TAT TGG CAT GCA AGC TAC GCG CTT AAT TCG TAC TGG         2292
Pro Val Ser Ile Tyr Trp His Ala Ser Tyr Ala Leu Asn Ser Tyr Trp
        430                 435                 440

GCT CAG TTT CGT AAC CAA AGC ATT CAA TGT TTC TTC AAT GGA TTG GCT         2340
Ala Gln Phe Arg Asn Gln Ser Ile Gln Cys Phe Phe Asn Gly Leu Ala
    445                 450                 455

CAT GAG ACA ACA ACC AAC CCT  G GTGAGCCATT CTTTGTAGTT TCCAAATTTA         2392
His Glu Thr Thr Thr Asn Pro
460                 465

GACCAAAATA ACCTTTTCGT ATAGTCACTA ACAAAGATTT TTTACAG  GA AAT GAT         2447
                                                     Gly Asn Asp

CGT TGC AAG TTT CCG AGC GTT ACT CTG TGAGGAGGAC TTGAGGAAGA               2494
Arg Cys Lys Phe Pro Ser Val Thr Leu
            470                 475

AGACACATGA TTAAAGCTGG ATTATTCGTA TAACTCAATA ATGTTCCTTA TCTTTTTTTT       2554

TATTATACCT TTTTT                                                        2569

(2) INFORMATION FOR SEQ ID NO: 20:

(i) SEQUENCE CHARACTERISTICS:
        (A) LENGTH: 478 amino acids
        (B) TYPE: amino acid
        (D) TOPOLOGY: linear (ii) MOLECULE TYPE: protein (xi) SEQUENCE DESCRIPTION: SEQ ID NO: 20:

Met Ser Leu Leu Ala Phe Phe Leu Phe Thr Ile Leu Val Phe Ser Ser
 1               5                  10                  15

Ser Cys Cys Ser Ala Thr Arg Phe Gln Gly His Arg Tyr Met Gln Arg
            20                  25                  30

Lys Thr Met Leu Asp Leu Ala Ser Lys Ile Gly Ile Asn Tyr Gly Arg
        35                  40                  45

Arg Gly Asn Asn Leu Pro Ser Pro Tyr Gln Ser Ile Asn Phe Ile Lys
    50                  55                  60
```

```
Ser Ile Lys Ala Gly His Val Lys Leu Tyr Asp Ala Asp Pro Glu Ser
 65                  70                  75                  80

Leu Thr Leu Leu Ser Gln Thr Asn Leu Tyr Val Thr Ile Thr Val Pro
                 85                  90                  95

Asn His Gln Ile Thr Ala Leu Ser Asn Gln Thr Ile Ala Asp Glu
            100                 105                 110

Trp Val Arg Thr Asn Ile Leu Pro Tyr Tyr Pro Gln Thr Gln Ile Arg
            115                 120                 125

Phe Val Leu Val Gly Asn Glu Ile Leu Ser Tyr Asn Ser Gly Asn Val
130                 135                 140

Ser Val Asn Leu Val Pro Ala Met Arg Lys Ile Val Asn Ser Leu Arg
145                 150                 155                 160

Leu His Gly Ile His Asn Ile Lys Val Gly Thr Pro Leu Ala Met Asp
                165                 170                 175

Ser Leu Arg Ser Ser Phe Pro Arg Ser Asn Gly Thr Phe Arg Glu Glu
            180                 185                 190

Ile Thr Gly Pro Val Met Leu Pro Leu Leu Lys Phe Leu Asn Gly Thr
            195                 200                 205

Asn Ser Tyr Phe Phe Leu Asn Val His Pro Tyr Phe Arg Trp Ser Arg
    210                 215                 220

Asn Pro Met Asn Thr Ser Leu Asp Phe Ala Leu Phe Gln Gly His Ser
225                 230                 235                 240

Thr Tyr Thr Asp Pro Gln Thr Gly Leu Val Tyr Arg Asn Leu Leu Asp
                245                 250                 255

Gln Met Leu Asp Ser Val Leu Phe Ala Met Thr Lys Leu Gly Tyr Pro
            260                 265                 270

His Met Arg Leu Ala Ile Ser Glu Thr Gly Trp Pro Asn Phe Gly Asp
            275                 280                 285

Ile Asp Glu Thr Gly Ala Asn Ile Leu Asn Ala Thr Tyr Asn Arg
            290                 295                 300

Asn Leu Ile Lys Lys Met Ser Ala Ser Pro Ile Gly Thr Pro Ser
305                 310                 315                 320

Arg Pro Gly Leu Pro Ile Pro Thr Phe Val Phe Ser Leu Phe Asn Glu
                325                 330                 335

Asn Gln Lys Ser Gly Ser Gly Thr Gln Arg His Trp Gly Ile Phe Asp
            340                 345                 350

Pro Asp Gly Ser Pro Ile Tyr Asp Val Asp Phe Thr Gly Gln Thr Pro
            355                 360                 365

Leu Thr Gly Phe Asn Pro Leu Pro Lys Pro Thr Asn Asn Val Pro Tyr
370                 375                 380

Lys Gly Gln Val Trp Cys Val Pro Val Glu Gly Ala Asn Glu Thr Glu
385                 390                 395                 400

Leu Glu Glu Thr Leu Arg Met Ala Cys Ala Gln Ser Asn Thr Thr Cys
                405                 410                 415

Ala Ala Leu Ala Pro Gly Arg Glu Cys Tyr Glu Pro Val Ser Ile Tyr
            420                 425                 430

Trp His Ala Ser Tyr Ala Leu Asn Ser Tyr Trp Ala Gln Phe Arg Asn
            435                 440                 445

Gln Ser Ile Gln Cys Phe Phe Asn Gly Leu Ala His Glu Thr Thr Thr
    450                 455                 460

Asn Pro Gly Asn Asp Arg Cys Lys Phe Pro Ser Val Thr Leu
465                 470                 475
```

(2) INFORMATION FOR SEQ ID NO: 21:

(i) SEQUENCE CHARACTERISTICS:
    (A) LENGTH: 1708 base pairs
    (B) TYPE: nucleic acid
    (C) STRANDEDNESS: single
    (D) TOPOLOGY: linear (ii) MOLECULE TYPE: DNA (genomic)

(vi) ORIGINAL SOURCE:
    (A) ORGANISM: Arabidopsis thaliana A6

(xi) SEQUENCE DESCRIPTION: SEQ ID NO: 21:

```
CCAGACACAA ACACAAAGAC ATGTCTCTTC TTGCTTTCTT CCTCTTCACC ATCCTTGTCT      60

TTTCAAGTAA GTCATCTTAA TAATGCATCA TGTTTACATT TTCTTTACGT AATCTCCCAT     120

ATTGAACATG GTTTTCTTGG TTTTACAGGT TCATGTTGTT CCGCAACTCG GTTCCAAGGG     180

CACAGGTACA TGCAGAGGAA AACAATGCTA GATTTGGCTA GCAAGATTGG TATCAACTAT     240

GGAAGAAGAG GAAACAACCT CCCATCTCCA TATCAATCCA TCAACTTCAT CAAATCTATC     300

AAAGCTGGTC ATGTCAAGCT CTATGACGCC GATCCAGAGA GTCTCACACT CCTCTCTCAA     360

ACCAATCTCT ACGTCACCAT AACCGTCCCT AACCACCAAA TCACCGCCCT CAGCTCTAAC     420

CAAACCATAG CTGACGAATG GGTCAGAACT AACATCCTCC CTTACTATCC ACAAACACAA     480

ATCCGTTTTG TCCTTGTCGG AAACGAAATC CTCAGCTACA ATTCTGGGAA TGTCTCTGTG     540

AATCTTGTAC CGGCGATGCG CAAGATCGTT AACTCACTCA GATTACATGG GATTCACAAC     600

ATCAAAGTTG GACACCTCT AGCTATGGAT TCTCTCCGGT CGTCGTTTCC TCGATCGAAC      660

GGAACATTCC GGGAAGAAAT CACCGGACCG GTGATGTTAC CGTTGCTGAA GTTTCTCAAC     720

GGAACAAACT CTTACTTCTT CCTTAATGTT CATCCTTACT TCCGTTGGTC AAGAAACCCC     780

ATGAACACCA GTTTGGATTT TGCTCTGTTC CAAGGACACT CAACCTATAC CGATCCTCAA     840

ACCGGTTTGG TTTACCGTAA TCTTCTAGAC CAAATGTTGG ATTCGGTTCT CTTCGCCATG     900

ACCAAACTCG GTTATCCACA TATGCGCCTC GCGATCTCTG AAACCGGATG GCCTAATTTC     960

GGTGACATCG ACGAAACCGG AGCCAACATT CTCAACGCAG CTACCTATAA CCGTAATCTG    1020

ATCAAGAAGA TGAGCGCAAG TCCTCCAATC GGTACACCAT CAAGACCCGG TTTACCAATA    1080

CCGACATTTG TTTTCTCCTT ATTCAACGAA ACCAGAAAT CCGGTTCGGG GACACAGAGA     1140

CATTGGGGAA TCTTCGATCC CGACGGTTCA CCAATCTACG ACGTAGATTT CACCGGTCAA    1200

ACACCCTTAA CCGGTTTCAA CCCGTTACCT AAACCGACGA ACAACGTTCC TTACAAAGGT    1260

CAAGTGTGGT GCGTACCAGT CGAAGGAGCC AACGAGACTG AGCTTGAAGA AACATTGAGG    1320

ATGGCTTGTG CCCAAAGCAA CACCACTTGT GCAGCTTTAG CTCCTGGGAG AGAATGTTAC    1380

GAACCAGTCT CCATTTATTG GCATGCAAGC TACGCGCTTA ATTCGTACTG GGCTCAGTTT    1440

CGTAACCAAA GCATTCAATG TTTCTTCAAT GGATTGGCTC ATGAGACAAC AACCAACCCT    1500

GGTGAGCCAT TCTTTGTAGT TTCCAAATTT AGACCAAAAT AACCTTTTCG TATAGTCACT    1560

AACAAAGATT TTTTACAGGA AATGATCGTT GCAAGTTTCC GAGCGTTACT CTGTGAGGAG    1620

GACTTGAGGA AGAAGACACA TGATTAAAGC TGGATTATTC GTATAACTCA ATAATGTTCC    1680

TTATCTTTTT TTTTATTATA CCTTTTTT                                        1708
```

(2) INFORMATION FOR SEQ ID NO: 22:

(i) SEQUENCE CHARACTERISTICS:
        (A) LENGTH: 1484 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
         (A) ORGANISM: Brassica napus A6

(xi) SEQUENCE DESCRIPTION: SEQ ID NO: 22:

| | | | | | |
|---|---|---|---|---|---|
| CTTTCTTCCT | CTTCACCCTC | GTCGTCTTTT | CAAGTACAAG | TTGCTCAGCG | GTTGGGTTCC | 60
| AACATCCGCA | CAGGTATATA | CAGAAAAAAA | CGATGCTAGA | GTTAGCCAGC | AAGATTGGTA | 120
| TTAACTATGG | TAGACAAGGA | ACAACCTAC  | CATCTCCTTA | CCAATCGATC | AATTTCATCA | 180
| AACTCATCAA | AGCCGGTCAT | GTCAAGCTCT | ACGACGCCGA | TCCAGAGAGT | CTAACACTCC | 240
| TCTCTCAAAC | CAATCTCTAC | GTCACCATAG | CGGTGCCAAC | CCACCAGATC | ACTTCCCTCA | 300
| GCGCCAACCA | AACTACAGCT | GAAGATTGGG | TCAAAACCAA | TATCCTCCCT | TACTACCCAC | 360
| AAACACAAAT | ACGATTTGTC | CTTGTTGGAA | ACGAAATCCT | CTCCGTCAAA | GATAGGAACA | 420
| TAACCGGCAA | TGTCGTACCG | GCAATGCGAA | AAATCGTGAA | CTCTCTCAGA | GCCCATGGGA | 480
| TTCACAACAT | CAAAGTCGGT | ACACCTTTAG | CTATGGATTC | TCTTCGATCA | ACGTTTCCGC | 540
| CGTCGAACTC | AACATTCCGG | GGAGATATCG | CCTTACCGTT | AATGTTGCCG | TTGCTGAAGT | 600
| TTCTCAACGG | AACAAACTCT | TACTTCTTTA | TCAATCTTCA | ACCTTACTTC | CGTTGGTCAA | 660
| GAAACCCTAA | TCACACCACG | TTGGATTTCG | CTCTGTTTCA | AGGAAACTCA | ACTTATACCG | 720
| ATCCTCATAC | CGGTTTGGTT | TACCATAATC | TTGTAGACCA | AATGTTGGAT | TCGGTTATCT | 780
| TCGCCATGAC | CAAGCTCGGT | TATCCATACA | TCCGTATCGC | AATCTCTGAA | ACCGGATGGC | 840
| CTAACTCCGG | CGACATCGAC | GAAATCGGAG | CTAACGTTTT | CAACGCCGCC | ACGTATAACC | 900
| GGAATTTGAT | CAAGAAGATG | ACCGCAACTC | CACCAATCGG | TACACCAGCT | AGACCCGGTT | 960
| CACCTATACC | GACATTTGTT | TTCTCCTTAT | TTAACGAAAA | CAAGAAACCC | GGTTCGGGAA | 1020
| CACAAAGACA | TTGGGGAATC | TTGCATCCGG | ACGGTACACC | AATCTACGAC | ATTGATTTTA | 1080
| CCGGTCAAAA | ACCCTTAACC | GGTTTTAACC | CTCTGCCTAA | ACCGACGAAT | AACGTTCCTT | 1140
| ACAAGGGTCA | AGTGTGGTGC | GTACCGGTCG | AAGGAGCCAA | CGAGACTGAG | CTCGAGGAAG | 1200
| CTTTGAGGAT | GGCTTGTGCC | CGAAGCAACA | CGACGTGTGC | GGCTTTGGTT | CCTGGCAGAG | 1260
| AATGTTACGA | GCCGGTCTCT | GTTTATTGGC | ACGAAGCTA  | CGCGCTTAAC | TCGTACTGGG | 1320
| CACAGTTCCG | TAGCCAAAAC | GTCCAATGTT | ACTTCAATGG | ATTAGCTCAT | GAGACCACGA | 1380
| CTAACCCTGG | AAATGATCGC | TGCAAGTTTC | CGAGCGTTAC | TCTGTGAGGA | AGAACGCCTG | 1440
| AAAGAGATTT | AAGATGATCA | AAGCTGGATT | ATTCGTATTT | ACTC       |            | 1484

(2) INFORMATION FOR SEQ ID NO: 23:

(i) SEQUENCE CHARACTERISTICS:
        (A) LENGTH: 478 amino acids
        (B) TYPE: amino acid
        (C) STRANDEDNESS: single
        (D) TOPOLOGY: linear (ii) MOLECULE TYPE: peptide (vi) ORIGINAL SOURCE:
         (A) ORGANISM: Arabidopsis thaliana A6

(xi) SEQUENCE DESCRIPTION: SEQ ID NO: 23:

```
Met Ser Leu Leu Ala Phe Phe Leu Phe Thr Ile Leu Val Phe Ser Ser
1               5                   10                  15

Ser Cys Cys Ser Ala Thr Arg Phe Gln Gly His Arg Tyr Met Gln Arg
                20                  25                  30
```

```
Lys Thr Met Leu Asp Leu Ala Ser Lys Ile Gly Ile Asn Tyr Gly Arg
         35                  40                  45

Arg Gly Asn Asn Leu Pro Ser Pro Tyr Gln Ser Ile Asn Phe Ile Lys
 50                  55                  60

Ser Ile Lys Ala Gly His Val Lys Leu Tyr Asp Ala Asp Pro Glu Ser
 65                  70                  75                  80

Leu Thr Leu Leu Ser Gln Thr Asn Leu Tyr Val Thr Ile Thr Val Pro
                 85                  90                  95

Asn His Gln Ile Thr Ala Leu Ser Ser Asn Gln Thr Ile Ala Asp Glu
                100                 105                 110

Trp Val Arg Thr Asn Ile Leu Pro Tyr Pro Gln Thr Gln Ile Arg
            115                 120                 125

Phe Val Leu Val Gly Asn Glu Ile Leu Ser Tyr Asn Ser Gly Asn Val
130                 135                 140

Ser Val Asn Leu Val Pro Ala Met Arg Lys Ile Val Asn Ser Leu Arg
145                 150                 155                 160

Leu His Gly Ile His Asn Ile Lys Val Gly Thr Pro Leu Ala Met Asp
                165                 170                 175

Ser Leu Arg Ser Ser Phe Pro Arg Ser Asn Gly Thr Phe Arg Glu Glu
            180                 185                 190

Ile Thr Gly Pro Val Met Leu Pro Leu Leu Lys Phe Leu Asn Gly Thr
        195                 200                 205

Asn Ser Tyr Phe Phe Leu Asn Val His Pro Tyr Phe Arg Trp Ser Arg
210                 215                 220

Asn Pro Met Asn Thr Ser Leu Asp Phe Ala Leu Phe Gln Gly His Ser
225                 230                 235                 240

Thr Tyr Thr Asp Pro Gln Thr Gly Leu Val Tyr Arg Asn Leu Leu Asp
                245                 250                 255

Gln Met Leu Asp Ser Val Leu Phe Ala Met Thr Lys Leu Gly Tyr Pro
            260                 265                 270

His Met Arg Leu Ala Ile Ser Glu Thr Gly Trp Pro Asn Phe Gly Asp
        275                 280                 285

Ile Asp Glu Thr Gly Ala Asn Ile Leu Asn Ala Ala Thr Tyr Asn Arg
290                 295                 300

Asn Leu Ile Lys Lys Met Ser Ala Ser Pro Pro Ile Gly Thr Pro Ser
305                 310                 315                 320

Arg Pro Gly Leu Pro Ile Pro Thr Phe Val Phe Ser Leu Phe Asn Glu
                325                 330                 335

Asn Gln Lys Ser Gly Ser Gly Thr Gln Arg His Trp Gly Ile Phe Asp
            340                 345                 350

Pro Asp Gly Ser Pro Ile Tyr Asp Val Asp Phe Thr Gly Gln Thr Pro
        355                 360                 365

Leu Thr Gly Phe Asn Pro Leu Pro Lys Pro Thr Asn Asn Val Pro Tyr
370                 375                 380

Lys Gly Gln Val Trp Cys Val Pro Val Glu Gly Ala Asn Glu Thr Glu
385                 390                 395                 400

Leu Glu Glu Thr Leu Arg Met Ala Cys Ala Gln Ser Asn Thr Thr Cys
                405                 410                 415

Ala Ala Leu Ala Pro Gly Arg Glu Cys Tyr Glu Pro Val Ser Ile Tyr
            420                 425                 430

Trp His Ala Ser Tyr Ala Leu Asn Ser Tyr Trp Ala Gln Phe Arg Asn
        435                 440                 445

Gln Ser Ile Gln Cys Phe Phe Asn Gly Leu Ala His Glu Thr Thr Thr
450                 455                 460
```

Asn Pro Gly Asn Asp Arg Cys Lys Phe Pro Ser Val Thr Leu
465                 470                 475

(2) INFORMATION FOR SEQ ID NO: 24:

(i) SEQUENCE CHARACTERISTICS:
        (A) LENGTH: 474 amino acids
        (B) TYPE: amino acid
        (C) STRANDEDNESS: single
        (D) TOPOLOGY: linear (ii) MOLECULE TYPE: peptide (vi) ORIGINAL SOURCE:
        (A) ORGANISM: Brassica napus A6

(xi) SEQUENCE DESCRIPTION: SEQ ID NO: 24:

Phe Phe Leu Phe Thr Leu Val Val Phe Ser Ser Thr Ser Cys Ser Ala
1               5                   10                  15

Val Gly Phe Gln His Pro His Arg Tyr Ile Gln Lys Lys Thr Met Leu
            20                  25                  30

Glu Leu Ala Ser Lys Ile Gly Ile Asn Tyr Gly Arg Gln Gly Asn Asn
        35                  40                  45

Leu Pro Ser Pro Tyr Gln Ser Ile Asn Phe Ile Lys Leu Ile Lys Ala
50                  55                  60

Gly His Val Lys Leu Tyr Asp Ala Asp Pro Glu Ser Leu Thr Leu Leu
65                  70                  75                  80

Ser Gln Thr Asn Leu Tyr Val Thr Ile Thr Val Pro Asn His Gln Ile
                85                  90                  95

Thr Ser Leu Ser Ala Asn Gln Thr Thr Ala Glu Asp Trp Val Lys Thr
            100                 105                 110

Asn Ile Leu Pro Tyr Tyr Pro Gln Thr Gln Ile Arg Phe Val Leu Val
        115                 120                 125

Gly Asn Glu Ile Leu Ser Val Lys Asp Arg Asn Ile Thr Gly Asn Val
130                 135                 140

Val Pro Ala Met Arg Lys Ile Val Asn Ser Leu Arg Ala His Gly Ile
145                 150                 155                 160

His Asn Ile Lys Val Gly Thr Pro Leu Ala Met Asp Ser Leu Arg Ser
                165                 170                 175

Thr Phe Pro Pro Ser Asn Ser Thr Phe Arg Gly Asp Ile Ala Leu Pro
            180                 185                 190

Leu Met Leu Pro Leu Leu Lys Phe Leu Asn Gly Thr Asn Ser Tyr Phe
        195                 200                 205

Phe Ile Asn Leu Gln Pro Tyr Phe Arg Trp Ser Arg Asn Pro Asn His
210                 215                 220

Thr Thr Leu Asp Phe Ala Leu Phe Gln Gly Asn Ser Thr Tyr Thr Asp
225                 230                 235                 240

Pro His Thr Gly Leu Val Tyr His Asn Leu Val Asp Gln Met Leu Asp
                245                 250                 255

Ser Val Ile Phe Ala Met Thr Lys Leu Gly Tyr Pro Tyr Ile Arg Ile
            260                 265                 270

Ala Ile Ser Glu Thr Gly Trp Pro Asn Ser Gly Asp Ile Asp Glu Ile
        275                 280                 285

Gly Ala Asn Val Phe Asn Ala Ala Thr Tyr Asn Arg Asn Leu Ile Lys
290                 295                 300

Lys Met Thr Ala Thr Pro Pro Ile Gly Thr Pro Ala Arg Pro Gly Ser
305                 310                 315                 320

```
Pro Ile Pro Thr Phe Val Phe Ser Leu Phe Asn Glu Asn Lys Lys Pro
            325                 330                 335

Gly Ser Gly Thr Gln Arg His Trp Gly Ile Leu His Pro Asp Gly Thr
            340                 345                 350

Pro Ile Tyr Asp Ile Asp Phe Thr Gly Gln Lys Pro Leu Thr Gly Phe
            355                 360                 365

Asn Pro Leu Pro Lys Pro Thr Asn Asn Val Pro Tyr Lys Gly Gln Val
    370                 375                 380

Trp Cys Val Pro Val Glu Gly Ala Asn Glu Thr Glu Leu Glu Glu Ala
385                 390                 395                 400

Leu Arg Met Ala Cys Ala Arg Ser Asn Thr Thr Cys Ala Ala Leu Val
                405                 410                 415

Pro Gly Arg Glu Cys Tyr Glu Pro Val Ser Val Tyr Trp His Ala Ser
                420                 425                 430

Tyr Ala Leu Asn Ser Tyr Trp Ala Gln Phe Arg Ser Gln Asn Val Gln
            435                 440                 445

Cys Tyr Phe Asn Gly Leu Ala His Glu Thr Thr Thr Asn Pro Gly Asn
    450                 455                 460

Asp Arg Cys Lys Phe Pro Ser Val Thr Leu
465                 470
```